(12) United States Patent
West et al.

(10) Patent No.: US 8,841,342 B2
(45) Date of Patent: Sep. 23, 2014

(54) CARRIER

(75) Inventors: Simon Michael West, Williamstown (AU); David Kannar, Belgrave South (AU)

(73) Assignee: Vital Health Sciences Pty. Ltd., Melbourne (AU)

( * ) Notice: Subject to any disclaimer, the term of this patent is extended or adjusted under 35 U.S.C. 154(b) by 1766 days.

(21) Appl. No.: 10/524,090

(22) PCT Filed: Aug. 7, 2003

(86) PCT No.: PCT/AU03/00998
§ 371 (c)(1), (2), (4) Date: Jul. 5, 2006

(87) PCT Pub. No.: WO2004/014432
PCT Pub. Date: Feb. 19, 2004

(65) Prior Publication Data
US 2006/0257459 A1 Nov. 16, 2006

(30) Foreign Application Priority Data
Aug. 9, 2002 (AU) ............................... 2002950713

(51) Int. Cl.
| | | |
|---|---|---|
| *A61K 31/355* | (2006.01) | |
| *A61K 47/48* | (2006.01) | |
| *A61K 31/485* | (2006.01) | |
| *A61K 31/568* | (2006.01) | |
| *A61K 31/46* | (2006.01) | |
| *A61K 47/24* | (2006.01) | |
| *A61K 31/565* | (2006.01) | |
| *A61K 9/00* | (2006.01) | |

(52) U.S. Cl.
CPC ......... *A61K 47/48084* (2013.01); *A61K 31/485* (2013.01); *A61K 31/568* (2013.01); *A61K 31/46* (2013.01); *A61K 47/24* (2013.01); *A61K 31/565* (2013.01); *A61K 9/0014* (2013.01)
USPC ....................................................... 514/458

(58) Field of Classification Search
None
See application file for complete search history.

(56) References Cited

U.S. PATENT DOCUMENTS

| | | |
|---|---|---|
| 2,407,823 A | 9/1946 | Fieser |
| 2,667,479 A | 1/1954 | Hoffman et al. |
| 2,913,477 A | 11/1959 | Hirschmann |
| 3,127,434 A | 3/1964 | Andrews |
| 3,212,901 A | 10/1965 | Robeson |
| 4,075,333 A | 2/1978 | Josse |
| 4,141,938 A | 2/1979 | Klose |
| 4,299,906 A | 11/1981 | Liu |
| 4,369,172 A | 1/1983 | Schor et al. |
| 4,444,755 A | 4/1984 | Horrobin |
| 4,603,142 A | 7/1986 | Burger et al. |
| 4,654,373 A | 3/1987 | Bertelli |
| 4,684,520 A | 8/1987 | Bertelli |
| 4,686,211 A | 8/1987 | Hara et al. |
| 4,874,883 A | 10/1989 | Uphues et al. |
| 4,952,495 A | 8/1990 | Belly et al. |
| 5,041,434 A | 8/1991 | Lubkin |
| 5,053,222 A | 10/1991 | Takasu et al. |
| 5,091,848 A | 2/1992 | Kojima |
| 5,094,848 A | 3/1992 | Brixner |
| 5,114,957 A | 5/1992 | Hendler et al. |
| 5,138,084 A | 8/1992 | Casagrande et al. |
| 5,173,304 A | 12/1992 | Lohner et al. |
| 5,334,378 A | 8/1994 | Mitani et al. |
| 5,374,645 A | 12/1994 | Kurihara-Bergstrom et al. |
| 5,387,579 A | 2/1995 | Meybeck et al. |
| 5,446,070 A | 8/1995 | Mantelle |
| 5,474,891 A | 12/1995 | Murphy |
| 5,474,991 A | 12/1995 | Ogata et al. |
| 5,554,781 A | 9/1996 | Reierson |
| 5,570,504 A | 11/1996 | Distefano et al. |
| 5,583,105 A | 12/1996 | Kovacs et al. |
| 5,589,504 A | 12/1996 | Dannenberg et al. |
| 5,603,949 A | 2/1997 | Meybeck et al. |
| 5,607,921 A | 3/1997 | Bernard et al. |
| 5,643,597 A | 7/1997 | Meybeck et al. |
| 5,656,618 A | 8/1997 | Meybeck et al. |
| 5,741,518 A | 4/1998 | Ribier et al. |
| 5,759,526 A | 6/1998 | Simonnet et al. |
| 5,776,915 A | 7/1998 | Peterson et al. |
| 5,780,504 A | 7/1998 | Ptchelintsev |
| 5,804,168 A | 9/1998 | Murad |

(Continued)

FOREIGN PATENT DOCUMENTS

| | | |
|---|---|---|
| CA | 1337992 | 1/1996 |
| CA | 2426852 | 5/2002 |

(Continued)

OTHER PUBLICATIONS

Brandt, Steroid hormone biosynthesis, Feb. 1, 2002, printed from http://www.rose-hulman.edu/—brandt/Chem430/Steroids.pdf on Nov. 20, 2010, 7 pages.*

(Continued)

*Primary Examiner* — Gigi Huang
(74) *Attorney, Agent, or Firm* — Michael Best & Friedrich LLP

(57) ABSTRACT

There is provided a method for improving the efficacy and/or transdermal transport of topically administered pharmaceuticals and pharmacologically active compounds, said method comprising the step of incorporating the pharmaceutical or pharmacologically active compound in a carrier comprising an effective amount of one or more complexes of a phosphate derivative of a lipophilic pharmaceutically acceptable compound.

11 Claims, 9 Drawing Sheets

(56) References Cited

U.S. PATENT DOCUMENTS

| | | | |
|---|---|---|---|
| 5,804,216 A | 9/1998 | Terren et al. | |
| 5,807,542 A | 9/1998 | Challis et al. | |
| 5,807,845 A | 9/1998 | Ogata et al. | |
| 5,885,595 A | 3/1999 | Corey et al. | |
| 5,906,811 A | 5/1999 | Hersh | |
| 5,908,846 A | 6/1999 | Bundgaard et al. | |
| 5,916,915 A | 6/1999 | Hong et al. | |
| 5,928,631 A | 7/1999 | Lucas et al. | |
| 5,952,361 A | 9/1999 | Dias Nahoum | |
| 5,952,373 A | 9/1999 | Lanzendorfer et al. | |
| 5,965,750 A * | 10/1999 | Oonishi et al. | 549/218 |
| 5,981,474 A | 11/1999 | Manning et al. | |
| 6,022,867 A | 2/2000 | Ito et al. | |
| 6,028,105 A | 2/2000 | Nigra | |
| 6,046,181 A | 4/2000 | Oonishi et al. | |
| 6,048,891 A | 4/2000 | Wechter | |
| 6,096,326 A | 8/2000 | Wikholm | |
| 6,121,249 A | 9/2000 | Weissman et al. | |
| 6,143,770 A | 11/2000 | Lane et al. | |
| 6,184,247 B1 | 2/2001 | Schneider | |
| 6,231,885 B1 | 5/2001 | Carrara | |
| 6,248,758 B1 | 6/2001 | Klokkers et al. | |
| 6,248,779 B1 * | 6/2001 | Shimizu et al. | 514/458 |
| 6,361,800 B1 | 3/2002 | Cooper et al. | |
| 6,384,043 B1 | 5/2002 | Peyman et al. | |
| 6,403,811 B1 | 6/2002 | West | |
| 6,417,223 B1 | 7/2002 | Sanders et al. | |
| 6,423,742 B1 | 7/2002 | Larson | |
| 6,444,220 B2 | 9/2002 | Wiley | |
| 6,444,234 B1 | 9/2002 | Kirby et al. | |
| 6,479,540 B1 | 11/2002 | Constantinides et al. | |
| 6,485,950 B1 | 11/2002 | Kumar et al. | |
| 6,503,545 B1 | 1/2003 | Perlman et al. | |
| 6,579,995 B1 | 6/2003 | West | |
| 6,599,933 B2 | 7/2003 | Takada et al. | |
| 6,641,847 B1 | 11/2003 | Nawar | |
| 6,645,998 B2 | 11/2003 | Sanders et al. | |
| 6,703,384 B2 | 3/2004 | Sanders et al. | |
| 6,727,280 B2 | 4/2004 | Palepu et al. | |
| 6,770,672 B1 | 8/2004 | Sanders et al. | |
| 7,074,825 B2 | 7/2006 | Mo et al. | |
| 7,179,486 B1 | 2/2007 | Mulye | |
| 2001/0006659 A1 | 7/2001 | Koike et al. | |
| 2001/0044462 A1 | 11/2001 | Hensley et al. | |
| 2002/0045765 A1 | 4/2002 | Kim et al. | |
| 2002/0127198 A1 | 9/2002 | Rothbard et al. | |
| 2002/0131994 A1 | 9/2002 | Schur et al. | |
| 2002/0132845 A1 | 9/2002 | Miller et al. | |
| 2002/0151467 A1 | 10/2002 | Leung | |
| 2003/0035812 A1 | 2/2003 | Ito et al. | |
| 2003/0109575 A1 | 6/2003 | Lambert et al. | |
| 2003/0157326 A1 | 8/2003 | Vaghefi et al. | |
| 2003/0206972 A1 | 11/2003 | Babish et al. | |
| 2004/0052754 A1 | 3/2004 | West et al. | |
| 2004/0067890 A1 | 4/2004 | Gupta | |
| 2004/0096493 A1 | 5/2004 | West | |
| 2004/0097431 A1 | 5/2004 | Sanders et al. | |
| 2004/0097472 A1 | 5/2004 | West et al. | |
| 2004/0131569 A1 * | 7/2004 | Schneider et al. | 424/70.1 |
| 2004/0167081 A1 | 8/2004 | Abbruzzese et al. | |
| 2004/0204343 A1 | 10/2004 | Fishman | |
| 2004/0234602 A1 | 11/2004 | Fischer et al. | |
| 2004/0235938 A1 | 11/2004 | Sanders et al. | |
| 2004/0241225 A1 | 12/2004 | West | |
| 2004/0253318 A1 * | 12/2004 | West et al. | 424/601 |
| 2005/0009787 A1 | 1/2005 | West et al. | |
| 2005/0089495 A1 | 4/2005 | West | |
| 2006/0241085 A1 | 10/2006 | West et al. | |
| 2006/0281715 A1 | 12/2006 | West | |
| 2006/0281716 A1 | 12/2006 | West et al. | |
| 2007/0042999 A1 | 2/2007 | West et al. | |
| 2007/0135390 A1 | 6/2007 | West et al. | |
| 2007/0141133 A1 | 6/2007 | Wang et al. | |
| 2008/0254073 A1 | 10/2008 | Chi | |
| 2009/0004166 A1 | 1/2009 | West et al. | |
| 2009/0005348 A1 | 1/2009 | Ogru et al. | |
| 2009/0036354 A1 | 2/2009 | Gavin et al. | |
| 2009/0104258 A1 | 4/2009 | Dumas et al. | |
| 2009/0186856 A1 | 7/2009 | West et al. | |
| 2009/0233881 A1 | 9/2009 | West et al. | |
| 2009/0239827 A1 | 9/2009 | Ogru et al. | |
| 2010/0076094 A1 | 3/2010 | West | |
| 2010/0209459 A1 | 8/2010 | West et al. | |
| 2010/0222305 A1 | 9/2010 | West et al. | |
| 2010/0261670 A1 | 10/2010 | West et al. | |
| 2011/0003774 A1 | 1/2011 | West et al. | |

FOREIGN PATENT DOCUMENTS

| | | |
|---|---|---|
| CA | 2426885 | 5/2002 |
| EP | 0171009 | 2/1986 |
| EP | 0324387 | 7/1989 |
| EP | 0338429 | 10/1989 |
| EP | 0430045 | 6/1991 |
| EP | 0430336 | 6/1991 |
| EP | 0436911 | 7/1991 |
| EP | 0565007 | 10/1993 |
| EP | 0574255 | 12/1993 |
| EP | 0617963 | 10/1994 |
| EP | 0641790 | 3/1995 |
| EP | 0643969 | 3/1995 |
| EP | 0661053 | 7/1995 |
| EP | 0669132 | 8/1995 |
| EP | 0669437 | 8/1995 |
| EP | 0674904 | 10/1995 |
| EP | 0679399 | 11/1995 |
| EP | 0680760 | 11/1995 |
| EP | 0681840 | 11/1995 |
| EP | 0684043 | 12/1995 |
| EP | 0699440 | 3/1996 |
| EP | 0826365 | 3/1998 |
| EP | 0845216 | 6/1998 |
| EP | 0699437 | 12/1998 |
| EP | 0965328 | 12/1999 |
| EP | 1000541 | 5/2000 |
| EP | 1023897 | 8/2000 |
| EP | 1053749 | 11/2000 |
| EP | 1264595 | 12/2002 |
| GB | 778142 | 7/1957 |
| GB | 1121683 | 7/1968 |
| GB | 2227662 | 8/1990 |
| JP | 53015381 | 2/1978 |
| JP | 58180410 | 10/1983 |
| JP | 59044375 | 3/1984 |
| JP | 59157091 | 9/1984 |
| JP | 60197621 | 10/1985 |
| JP | 61086940 | 5/1986 |
| JP | 61091137 | 5/1986 |
| JP | 61176535 | 8/1986 |
| JP | 61233631 | 10/1986 |
| JP | 62195393 | 8/1987 |
| JP | 63093791 | 4/1988 |
| JP | 63139972 | 6/1988 |
| JP | 1228920 | 9/1989 |
| JP | 1274830 | 11/1989 |
| JP | 4208209 | 7/1992 |
| JP | 4270212 | 9/1992 |
| JP | 5132700 | 5/1993 |
| JP | 5201858 | 8/1993 |
| JP | 5509296 | 12/1993 |
| JP | 6048962 | 2/1994 |
| JP | 6056699 | 3/1994 |
| JP | 6502422 | 3/1994 |
| JP | 6078214 | 10/1994 |
| JP | 6508820 | 10/1994 |
| JP | 7011291 | 1/1995 |
| JP | 7207298 | 8/1995 |
| JP | 7507318 | 8/1995 |
| JP | 7278587 | 10/1995 |
| JP | 7316170 | 12/1995 |
| JP | 8073338 | 3/1996 |
| JP | 8193089 | 7/1996 |
| JP | 08231564 | 9/1996 |
| JP | 8311085 | 11/1996 |

(56) References Cited

FOREIGN PATENT DOCUMENTS

| | | |
|---|---|---|
| JP | 8311489 | 11/1996 |
| JP | 8325594 | 12/1996 |
| JP | 9044375 | 2/1997 |
| JP | 9309813 | 12/1997 |
| JP | 10045783 | 2/1998 |
| JP | 10155429 | 6/1998 |
| JP | 10509451 | 9/1998 |
| JP | 10511677 | 11/1998 |
| JP | 11043436 | 2/1999 |
| JP | 11506419 | 6/1999 |
| JP | 11199424 | 7/1999 |
| JP | 11199465 | 7/1999 |
| JP | 2000507557 | 6/2000 |
| JP | 2000198701 | 7/2000 |
| JP | 2001169731 | 6/2001 |
| JP | 2001247585 | 9/2001 |
| JP | 2002080475 | 3/2002 |
| JP | 2002088091 | 3/2002 |
| JP | 2003128531 | 5/2003 |
| JP | 2003171313 | 6/2003 |
| NZ | 244549 | 7/1994 |
| SU | 925961 | 5/1982 |
| WO | WO 91/17987 | 11/1991 |
| WO | WO 92/03122 | 3/1992 |
| WO | WO 92/07544 | 5/1992 |
| WO | WO 92/08459 | 5/1992 |
| WO | WO 92/15289 | 9/1992 |
| WO | WO 93/02661 | 2/1993 |
| WO | WO 93/15731 | 8/1993 |
| WO | WO 93/24131 | 12/1993 |
| WO | WO 95/31217 | 11/1995 |
| WO | WO 95/34303 | 12/1995 |
| WO | WO 96/17852 | 6/1996 |
| WO | 9621440 | 7/1996 |
| WO | WO 96/20715 | 7/1996 |
| WO | WO 96/29336 | 9/1996 |
| WO | 96/37196 | 11/1996 |
| WO | 97/02803 | 1/1997 |
| WO | WO 97/14705 | 4/1997 |
| WO | WO 97/35591 | 10/1997 |
| WO | WO 99/58555 | 11/1999 |
| WO | WO 00/08033 | 2/2000 |
| WO | WO 00/16772 | 3/2000 |
| WO | WO 00/30620 | 6/2000 |
| WO | WO 00/43380 | 7/2000 |
| WO | 00/44237 | 8/2000 |
| WO | 00/53728 | 9/2000 |
| WO | WO 00/57876 | 10/2000 |
| WO | WO 00/59475 | 10/2000 |
| WO | WO 00/69865 | 11/2000 |
| WO | WO 00/71094 | 11/2000 |
| WO | WO 00/71125 | 11/2000 |
| WO | 00/74684 | 12/2000 |
| WO | WO 01/19372 | 3/2001 |
| WO | WO 01/22937 | 4/2001 |
| WO | WO 01/35998 | 5/2001 |
| WO | WO 01/46204 | 6/2001 |
| WO | 01/54674 | 8/2001 |
| WO | WO 01/58889 | 8/2001 |
| WO | 01/72300 | 10/2001 |
| WO | WO 02/13810 | 2/2002 |
| WO | WO 02/26238 | 4/2002 |
| WO | 0240033 | 5/2002 |
| WO | 0240034 | 5/2002 |
| WO | WO 02/36736 | 5/2002 |
| WO | WO 02/39996 | 5/2002 |
| WO | 03011303 | 2/2003 |
| WO | WO 03/013550 | 2/2003 |
| WO | WO 03/024429 | 3/2003 |
| WO | WO 03/024430 | 3/2003 |
| WO | WO 03/026673 | 4/2003 |
| WO | 03/039461 | 5/2003 |
| WO | WO 03/043570 | 5/2003 |
| WO | 03049774 | 6/2003 |
| WO | 03/053407 | 7/2003 |
| WO | 03/068209 | 8/2003 |
| WO | 03/097714 | 11/2003 |
| WO | WO 03/101480 | 12/2003 |
| WO | WO 2004/014432 | 2/2004 |
| WO | WO 2004/060315 | 7/2004 |
| WO | WO 2004/064831 | 8/2004 |
| WO | WO 2004/091636 | 10/2004 |
| WO | WO 2004/092186 | 10/2004 |
| WO | WO 2004/092187 | 10/2004 |
| WO | WO 2005/023282 | 3/2005 |
| WO | WO 2005/084678 | 9/2005 |
| WO | WO 2006/012692 | 2/2006 |
| WO | WO 2006/092024 | 9/2006 |
| WO | WO 2006/092025 | 9/2006 |
| WO | WO 2006/133506 | 12/2006 |
| WO | WO 2007/070981 | 6/2007 |
| WO | 2009146443 | 12/2009 |

OTHER PUBLICATIONS

Morgan T. et al., "Enhanced Transdermal Delivery of Sex Hormones in Swine with a Novel Topical Aerosol", Journal of Pharmaceutical Sciences, vol. 87, No. 10, Oct. 1998, pp. 1219-1225.
Potts, R. et al., "Predicting Skin Permeability", Pharmaceutical Research, vol. 9, No. 5, 1992, pp. 663-669.
Ostrenga, J., et al. "Significance of Vehicle Composition I: Relationship between Topical Vehicle Composition, Skin Penetrability, and Clinical Efficacy", Journal of Pharmaceutical Sciences, vol. 60, 1971, pp. 1175-1179.
Barrett, C. et al., "The Effect of Particle Size and Vehicle on the Percutaneous Absorption of Fluocinolone Acetonide", Brit. J. Derm., vol. 77, 1965, pp. 576-578.
Nakayama, S. et al., "Protective effects of a stable, water-soluble vitamin E on photodamage induced by UVB irradiation in cultured mouse skin," Photomedicine and Photobiology (1998) 20:99-100.
United States Patent Office Action for U.S. Appl. No. 10/416,774 dated Dec. 18, 2009 (11 pages) document.
United States Patent Office Action for U.S. Appl. No. 10/542,511 dated Jan. 12, 2010 (13 pages) document.
Gann, P.H. et al., "Lower prostate cancer risk in men with elevated plasma lycopene levels: results of a prospective analysis," Cancer Res. (1999) 59(6):1225-1230.
Min, J. et al., "Effect of apoptosis induced by different vitamin E homologous analogues in human hepatoma cells (HepG2)," J. Hygiene Res. China (2003) 32(4):343-345.
Visarius, T. et al., "Inhibition of human prostate cancer cell proliferation: vitamin E and lycopene targeted pathways regulating cell cycle progression,"FASEB J. (2004) 18(8):C103.
Suzuki, T. et al., "The solution behavior and the association structure of long-chain monoalkyl phosphates," Chem. Soc. Japan (1986) 633-640, with English abstract.
United States Patent Office Action for U.S. Appl. No. 10/485,196 dated Jan. 25, 2010 (8 pages) Not a published document.
Iimura, N. et al., "Complex formation between cationic surfactants and insoluble drugs," Bull. Chem. Soc. Jpn. (1999) 72:2417-2422.
Imada, I. et al., "Photochemical reaction of ubiquinone. IV. Coenzymatic activity of ubiquinone and related compounds," Chem. Pharm. Bull. (1965) 13:136-142.
Gianello, R. et al., "α-tocopheryl phosphate: a novel, natural form of Vitamin E," Free Radical Biol. Med. (2005) 39:970-976.
Negis, Y. et al., "On the existence of cellular tocopheryl phosphate, its synthesis, degradation and cellular roles: a hypothesis," IUBMB Life (2005) 57(1):23-25.
Ogru, E. et al., "Vitamin E phosphate: an endogenous form of vitamin E," Medimond S.r.l. (2003) 127-132.
Traber, M.G. et al., "Human plasma vitamin E kinetics demonstrates rapid recycling of plasma RRR-alpha-tochopero," Proc. Natl. Acad. Sci. USA (1994) 91:10005-10008.
United States Office Action for U.S. Appl. No. 09/979,436 dated Apr. 4, 2002 (6 pages) Not a published document.
United States Office Action for U.S. Appl. No. 09/979,436 dated Sep. 23, 2002 (6 pages) Not a published document.
United States Office Action for U.S. Appl. No. 10/416,775 dated Nov. 2, 2005 (10 pages) Not a published document.

(56) References Cited

OTHER PUBLICATIONS

United States Office Action for U.S. Appl. No. 10/416,775 dated Jun. 12, 2006 (10 pages) Not a published document.
United States Office Action for U.S. Appl. No. 10/416,775 dated Jul. 12, 2007 (11 pages) Not a published document.
United States Office Action for U.S. Appl. No. 10/416,775 dated Dec. 17, 2008 (6 pages) Not a published document.
United States Office Action for U.S. Appl. No. 10/416,774 dated Sep. 6, 2007 (9 pages) Not a published document.
United States Office Action for U.S. Appl. No. 10/416,774 dated Jun. 11, 2008 (15 pages) Not a published document.
United States Office Actions for U.S. Appl. No. 10/416,774 dated Feb. 17, 2009 (15 pages) Not a published document.
United States Office Action for U.S. Appl. No. 10/416,774 dated Apr. 15, 2009 (14 pages) Not a published document.
United States Office Action for U.S. Appl. No. 10/462,480 dated Dec. 1, 2006 (10 pages) Not a published document.
United States Office Action for U.S. Appl. No. 10/462,480 dated Nov. 1, 2007 (10 pages) Not a published document.
United States Office Action for U.S. Appl. No. 10/462,480 dated Feb. 20, 2009 (17 pages) Not a published document.
United States Office Action for U.S. Appl. No. 10/485,196 dated May 29, 2008 (23 pages) Not a published document.
United States Office Action for U.S. Appl. No. 10/485,196 dated Jul. 23, 2009 (9 pages) Not a published document.
United States Office Action for U.S. Appl. No. 10/486,142 dated Mar. 18, 2008 (12 pages) Not a published document.
United States Office Action for U.S. Appl. No. 10/487,743 dated Dec. 2, 2005 (22 pages) Not a published document.
United States Office Action for U.S. Appl. No. 10/487,743 dated Jul. 27, 2006 (23 pages) Not a published document.
United States Office Action for U.S. Appl. No. 10/498,684 dated Oct. 2, 2008 (21 pages) Not a published document.
United States Office Action for U.S. Appl. No. 10/498,684 dated Jun. 23, 2009 (19 pages) Not a published document.
United States Office Action for U.S. Appl. No. 10/542,511 dated Aug. 8, 2007 (19 pages) Not a published document.
United States Office Action for U.S. Appl. No. 10/542,511 dated Mar. 31, 2008 (20 pages) Not a published document.
United States Office Action for U.S. Appl. No. 10/542,511 dated Feb. 5, 2009 (23 pages) Not a published document.
United States Office Action for U.S. Appl. No. 10/551,200 dated Jan. 28, 2009 (11 pages) Not a published document.
United States Office Action for U.S. Appl. No. 10/551,201 dated Jan. 24, 2008 (6 pages) Not a published document.
United States Office Action for U.S. Appl. No. 10/551,203 dated Dec. 6, 2006 (13 pages) Not a published document.
United States Office Action for U.S. Appl. No. 10/551,203 dated Sep. 7, 2007 (13 pages) Not a published document.
United States Office Action for U.S. Appl. No. 10/551,203 dated Apr. 11, 2008 (11 pages) Not a published document.
United States Office Action for U.S. Appl. No. 10/551,203 dated Dec. 19, 2008 (13 pages) Not a published document.
United States Office Action for U.S. Appl. No. 10/551,203 dated Jul. 21, 2009 (21 pages) Not a published document.
United States Patent Office Action for U.S. Appl. No. 11/817,453 dated Oct. 9, 2009 (11 pages) Not a published document.
United States Patent Office Action for U.S. Appl. No. 10/462,480 dated Nov. 27, 2009 (9 pages) Not a published document.
Aberg, F. et al., "Distribution and redox state of ubiquinones in rat and human tissues," Arch. Biochem. Biophys. (1992) 295(2):230-234.
Almeida, M.E.M. et al., "Evaluation of soybean oil deoderization distillate for Vitamin E recovery," Arq. Biol. Tecnol. (1994) 37(4):1003-1011.
Bikerman, J.J., "Mechanical destruction of young and old foam films," J. Phys. Chem. (1952) 56:164-165.
Blom, J.H. et al., "Reproductive success of female rainbow trout (*Oncorhynchus mykiss*) in response to graded dietary ascorbyl monophosphate levels," Biol. of Reproduction (1995) 52:1073-1080.

Cevc, G. "Transdermal drug delivery of insulin with ultradeformable carriers," Clin. Pharmacokinet. (2003) 42(5):461-474.
Cevc, G. et al., "Ultraflexible vesicles, transfersomes, have an extremely low pore penetration resistance and transport therapeutic amounts of insulin across the intact mammalian skin," Biochim. Biophys. Acta (1998) 1368:201-215.
De Wolfe, F.A. et al., "Ligand-binding proteins: their potential for application in systems for controlled delivery and uptake of ligands," Pharmacol. Rev. (2000) 52(2):207-236.
Devaraj, S. et al., "Modulation of monocyte-macrophage function with alpha-tocopherol: implications for atherosclerosis," Nat. Rev. (2002) 60(1):8-14.
Devaraj, S. et al., "Alpha tocopherol supplementation decreases serum C-reactive protein and monocyte interleukin-6 levels in normal volunteers and type 2 diabetic patients," Free Radic. Biol. Med. (2000) 29(8):790-792.
Ernster, L. et al., "Biochemical, physiological and medical aspects of ubiquinone function," Biochim. Biophys. Acta (1995) 1271:195-204.
Octoplus, "Formulation Development of Poorly Soluble Drugs" (www.octoplus.nl) (1999) 2 pages (downloaded Nov. 2008).
Fracalossi, D.M. et al., "Oscars, *Astronotus ocellatus*, have a dietary requirement for vitamin C," J. Nutrition (1998) 128:1745-1751.
Frei, B. et al., "Ubiquinol-10 is an effective lipid-soluble antioxidant at physiological concentrations," Proc. Natl. Acad. Sci. (1990) 87:4879-4883.
Godin, B. et al., "Ethosomes: new prospects in transdermal delivery," Crit. Rev. Thera. Drug Car. Syst. (2003) 20(1):63-102.
Goff et al., "Prevention of cardiovascular disease in persons with Type 2 diabetes mellitus: current knowledge and rationale for the action to control cardiovascular risk in diabetes (ACCORD) trial," Am. J. Cardiol. (2007) 99(suppl):4i-20i.
Griffin, E. et al., "A link between diabetes and atherosclerosis: glucose regulates expression of CD36 at the level of translation," Nature Med. (2001) 7(7):840-846.
Guo, J. et al., "Transdermal delivery of insulin in mice by using Lecithin vesicles as a carrier," Drug Del. (2000) 7:113-116.
Heron-Milhavet, L. et al., "Muscle-specific overexpression of CD36 reverses the insulin resistance and diabetes of MKR mice," Endocrinology (2004) 145:4667-4676.
Karrer, V.P. et al., "d,l-alpha-tocopherol-phosphorsaure-ester," Zurich, Chemisches Institut der Universitat (1933) p. 1137-1138, in German.
King, M.J. et al., "Transdermal delivery of insulin from a novel biphasic lipid system in diabetic rats," Diab. Tech. Therap. (2002) 4(4):479-488.
Knowler, W.C. et al., "Preventing Non-insulin-dependent diabetes," Diabetes (1995) 44:483-488.
Langsjoen, P.H. et al., "Overview of the use of CoQ10 in cardiovascular diseases," Biofactors (1999) 9:273-284.
Lass, A. et al., "Electron transport-linked ubiquinone-dependent recycling of α-tocopherol inhibits autooxidation of mitochondrial membranes," Arch. Biochem. Biophys. (1998) 352(2):229-236.
Lee, C-F. et al., "Attenuation of UV-induced apoptosis by coenzyme Q10 in human cells harboring large-scale deltion of mitochontrial DNA," Ann. N.Y. Acad. Sci. (2005) 1042:429-438.
Lei, B. et al.,. Progress in alpha-tocopherol preparation technology, Xiandai Huangong (1997) 17(7):13-15.
Maguire, J.J. et al., "Succinate-ubiquinone reductase linked recycling of alpha-tocopherol in reconstituted systems and mitochondria: requirement for reduced ubiquinone," Arch. Biochem. Biophys. (1992) 292(1):47-53.
Mellors, A. et al., "The inhibition of mitochondrial peroxidation by ubiquinone and ubiquinol," J. Biol. Chem. (1966) 241(19):4353-4356.
Merck Index, The, "α-estradiol" Thirteenth Edition, Whitehouse Station, NJ (2001) p. 660.
Merck Index, The, "Fludarabine to Fludeoxyglucose F18" pages, Thirteenth Edition, Whitehouse Station, NJ (2001) pp. 729-730.
Miyamoto, S. et al., "Synthesis of a novel phosphate ester of a vitamin E derivative and its antioxidative activity," Biosci. Biotech. Biochem. (1998) 62(12):2463-2466.

(56) References Cited

OTHER PUBLICATIONS

Morgan, T.M. et al., "Transdermal delivery of estradiol in postmenopausal women with a novel topical aerosol," J. Pharm. Sci. (1998) 87(10):1226-1228.
Mortensen, S.A., "Perspectives on therapy of cardiovascular diseases with coenzyme Q10 (ubiquinone)," Clin. Investig. (1993) 71(Suppl. 8):S116-S123.
Munteanu, A. et al., "Modulation of cell proliferation and gene expression by alpha-tocopheryl phosphates: relevance to atherosclerosis and inflammation," Biochem. Biophys. Res. Comm. (2004) 318(1):311-316.
Owens, D.R. et al., "Alternative routes of insulin delivery," Diabet. Med. (2003) 20:886-898.
Parker et al., "Neonatal vitamin K administration and childhood cancer in the North of England: retrospective case-control study," BMJ (1998) 316:189-193.
Puratchikody, A. et al., "Reverse phase—high performance liquid chromatographic determination of atorvastatin calcium in solid dosage forms," Pharma. Review (2003) 1(2):79-80, 83-STN File CA, Abstract 139:399976 only.
Sevast'Ianov, V.I. et al., "Transdermal delivery of insulin," Meditsinskaia Tekhnika (2003) 2:21-24.
Seyama, Y. et al., "Comparative effects of Vitamin K2 and estradiol on experimental arteriosclerosis with diabetes mellitus," Int. J. Vitam. Nutr. Res. (2000) 70(6):301-304, Absract only.
Singh, R.B. et al., "Randomized double-blind placebo-controlled trial of coenzyme Q10 in patients with acute myocardial infarction," Cardiov. Drugs Ther. (1998) 12:347-353.
Stedman's Medical Dictionary, "Tocopherol," "Tocotrienol," and "Vitamin K1", 22nd Edition, Williams & Wilkins Co. (1972) p. 1303 and 1400.
Younis et al., "The prevention of type 2 diabetes mellitus: recent advances," Q.J. Med. (2004) 97:451-455.
Gianello, R. et al., "Subchronic oral toxicity study of mixed tocopheryl phosphates in rats," Int'l J. Toxicol. (2007) 26:475-490.
Libinaki, R. et al., "Evaluation of the safety of mixed tocopheryl phosphates (MTP)-a formulation of α-tocopheryl phosphate plus α-di-tocopheryl phosphate," Food Chem. Toxicol. (2006) 44(7):916-932.
Little, P.J. et al., "Phosphorylated troglitazone activates PPARγ and inhibits vascular smooth muscle cell proliferation and proteoglycan synthesis," J. Cardiovasc. Pharmacol. (2008) 51(3):274-279.
Mukherjee, S. et al., "Cardioprotection with α-tocopheryl phosphate: amelioration of myocardial ischemia reperfusion injury is linked with its ability to generate a survival signal through Akt activation," Biochim. Biophys. Acta (2008) 1782:498-503.
Negis, Y. et al., "Molecular mechanism of alpha-tocopheryl-phospate transport across the cell membrane," Biochem. Biophys. Res. Comm. (2007) 359:348-353.
Negis, Y. et al., "The effect of tocopheryl phosphates on atherosclerosis progression in rabbits fed with a high cholesterol diet," Arch. Biochem. Biophys. (2006) 450:63-66.
Rerek, M.E. et al., "Disodium lauriminodipropionate tocopheryl phosphates: a potent new anti-inflammatory," Cosmetics & Toiletries magazine (2003) 118(7):63-67.
Rezk, B.M. et al., "The extraordinary antioxidant activity of vitamin E phosphate," Biochim. Biophys. Acta (2004) 1683:16-21.
United States Patent Office Action for U.S. Appl. No. 12/212,803 dated Mar. 12, 2010 (13 pages).
Japanese Patent Office Action for Application No. 2004-526500 dated Jan 26, 2010 (7 pages).
United States Patent Office Action for U.S. Appl. No. 11/817,453 dated Aug. 2, 2010 (10 pages).
United States Patent Office Action for U.S. Appl. No. 12/158,932 dated Aug. 19, 2010 (15 pages).
United States Patent Office Action for U.S. Appl. No. 10/498,684 dated Jul. 7, 2010 (21 pages).
Devaraj, S. et al., "Alpha tocopherol decreases CD36 expression in human monocyte—derived macrophages," J. Lipid Res. (2001) 42:521-527.
Ricciarelli, R. et al., "Vitamin E reduces the uptake of oxidized LDL by inhibiting CD36 scavenger receptor expression in cultured aortic smooth muscle cells," Circulation (2000) 102:82-87.
Teupser, D. et al., "Alpha-tocopherol down-regulates scavengers receptor activity in macrophages," Atherosclerosis (1999) 144:109-115.
United States Patent Office Action for U.S. Appl. No. 10/485,196 dated Oct. 29, 2010 (13 pages).
United States Patent Office Notice of Allowance for U.S. Appl. No. 12/628,443 dated Jan. 12, 2012 (7 pages).
United States Patent Office Action for U.S. Appl. No. 12/628,443 dated Feb. 18, 2011 (15 pages).
United States Patent Office Action for U.S. Appl. No. 12/768,307 dated Oct. 6, 2011 (13 pages).
United States Patent Office Action for U.S. Appl. No. 12/834,553 dated Oct. 7, 2011 (11 pages).
United States Patent Office Action for U.S. Appl. No. 12/690,735 dated Sep. 27, 2011 (15 pages).
United States Patent Office Action for U.S. Appl. No. 11/817,453 dated Oct. 13, 2011 (14 pages).
United States Patent Office Action for U.S. Appl. No. 11/917,831 dated Oct. 24, 2011 (11 pages).
United States Patent Office Action for U.S. Appl. No. 12/782,560 dated Sep. 1, 2011 (18 pages).
United States Patent Office Action for U.S. Appl. No. 12/782,564 dated Sep. 1, 2011 (10 pages).
United States Patent Office Action for U.S. Appl. No. 11/917,831 dated Jan. 9, 2011 (10 pages).
Jiang, Q. et al., "γ-tocopherol, the major form of vitamin E in the U.S. diet, deserves more attention," Am. J. Clin. Nutri. (2001) 74(6):714-722.
United States Patent Office Action for U.S. Appl. No. 11/817,439 dated Nov. 24, 2010 (15 pages).
United States Patent Office Action for U.S. Appl. No. 12/628,443 dated Aug. 5, 2011 (8 pages).
United States Patent Office Action for U.S. Appl. No. 11/817,439 dated Jul. 29, 2011 (2 pages).
Walters et al., "The effects of surfactants on penetration across the skin" International Journal of Cosmetic Science (1993), vol. 15, pp. 260-270.
United States Patent Office Action for U.S. Appl. No. 11/817,439 dated May 11, 2011 (11 pages).
Schwenke, D.C. et al., "α-tocopherol protects against diet induced atherosclerosis in New Zealand white rabbits," J. Lipid Res. (2002) 43:1927-1938.
United States Patent Office Notice of Allowance for U.S. Appl. No. 10/485,196 dated Apr. 14, 2011 (7 pages).
United States Patent Office Action for U.S. Appl. No. 12/834,553 dated Apr. 14, 2011 (13 pages).
United States Patent Office Action for U.S. Appl. No. 11/817,453 dated Mar. 9, 2011 (12 pages).
United States Patent Office Advisory Action for U.S. Appl. No. 10/542,511 dated May 25, 2010 (3 pages).

* cited by examiner

CARRIER

FIELD OF THE INVENTION

This invention relates to a carrier for use in the topical administration of pharmaceutical or pharmacologically active compounds.

BACKGROUND OF THE INVENTION

In this specification, where a document, act or item of knowledge is referred to or discussed, this reference or discussion is not to be taken as an admission that the document, act or item of knowledge was at the priority date: part of common general knowledge; or known to be relevant to an attempt to solve any problem with which this specification is concerned.

The major objective in drug delivery is to obtain an appropriate biological effect at a desired site of action. The choice of carrier can be critical to the efficacy of a topically delivered pharmaceutical or pharmacologically active compound. Bioactivity of a pharmaceutical will however, be sub-optimal if it does not possess the correct physiochemical properties to allow release of the biologically active form, from the formulation to the target site of action after passage across the skin.
Drug Transfer through the Skin When a drug is released from a formulation it will first partition into the outer lipids of the stratum corneum. The degree of absorption will depend primarily upon solubility of the drug into these lipids and partition co-efficient of the drug between the skin and the formulation. A simple method for maximizing this is to choose formulation components that allow the drug dose to reach its solubility limit. Ostrenga et al. demonstrated this principle by improving solubility and partition characteristics of two corticosteroids through manipulating the formulation ratio of water and propylene glycol, demonstrating that the most effective formulations were those that contained adequate propylene glycol to solubilize the maximum drug concentration in the finished pharmaceutical product (Ostrenga J. Steinmetz C, Poulsen B. Significance of vehicle composition 1. Relationship between topical vehicle composition, skin penetrability, and clinical efficacy. J. Pharm. Sci. 1971; 60:1175-1179).

It is also reported that supersaturated systems provide thermodynamic activity greater than unity that enhances skin penetration of drugs. A drug solvent system using a mixture of volatile and non-volatile solvents as vehicles, where the volatile compounds evaporate from the skin, can create a supersaturated solution on the skin surface and stimulate drug absorption. It is thought that some transdermal patch delivery systems have the ability to absorb water from the skin increasing thermodynamic activity of a drug creating a supersaturated solution thereby promoting its passage through the skin. One of the major problems with use of mixed volatile and non volatile delivery systems however, is the difficulty in creating systems that are reproducible, as the rate and degree of volatile evaporation will depend, to a large extent upon ambient conditions during application. Variability in absorption kinetics causes fluctuations in drug delivered and unreliable clinical efficacy.

When a suitable solvent system cannot be identified suspensions may be used. In these formulations, particle size of the incorporated drug compound can significantly influence effective absorption. This was demonstrated by Barrett et al. using a variety of fluocinolone acetonide formulations (Barrett C W, Hadgraft J W, Caron G A, Sarkany I. The effect of particle size and vehicle on the percutaneous absorption of fluocinolone acetonide. Brit. J. Dermatol 1965; 77:576-78). The formulations were applied to forearm skin of volunteers and degree of vasoconstriction measured. The effect was greatest in those formulations using micronized drug that had been taken into solution with propylene glycol. It was concluded that solubility and partition characteristics of a drug were dearly important parameters in formulating to promote skin absorption. In theory this means that drugs with good oil and water solubility and balanced partition coefficient, will better penetrate the skin.

Modern drugs typically do not have optimal solubility characteristics, and this is currently quantified by use of a solubility parameter. This has been estimated to be approximately for the skin, so drugs with solubility parameters similar to this may be expected to be freely soluble creating a large concentration gradient across the skin or high partition coefficient. The importance of this is evident in an analysis of skin permeability data by Potts and Guy (Potts R O, Guy R H. Predicting skin permeability. Pharm. Res. 1992; 9:663-669) who examined the permeability of 90 compounds in aqueous solution and determined that permeability coefficient ($K_p$) through the skin was related to their octanol-water partition coefficient and the molecular weight in the following relationship:

$$\text{Log } K_p \text{ (cm s}^{-1}\text{)} = -6.3 + 0.71 \log P - 0.0061 \, MW$$
$$(r^2 = 0.69)$$

This emphasizes the importance of solubility and partition coefficient, but like many mathematical structure activity relationships, results in a 2 dimensional answer to a three dimensional problem. For example, flux through the skin using this equation results in a parabolic dependency on the partition coefficient which is still unclear. If a true linear concentration gradient existed then the higher the concentration gradient, the higher the drug absorption. The fact that the relationship is not linear suggests that physical limits exist, such as the number of pores in the skin or physiochemical forces other than solubility, dissolution and dispersion which also act to facilitate membrane transport. It has been suggested that at high log P (a highly lipophilic compound), the transfer out of the stratum corneum is rate limiting or that drugs with high log P values generally have poor aqueous solubility. This means that lipid soluble drugs tend to stay in the phospholipid membrane because by nature they are lipophilic, that is, the drugs are trapped in the skin and not released to the target site.

Based on the equation and the accompanying assumption that drugs are transported across skin by virtue of a concentration gradient, it is suggested that drugs with log P in the range of 1 to 3 are more likely to diffuse through the skin. However, this simply serves to identify drugs that may move easily through the skin. This does not help to improve the transport of poorly soluble, highly lipophilic drugs.
Skin Enhancers Many modern drugs are highly lipophilic so skin enhancers and various formulation techniques have been developed to improve their absorption through the skin. Skin enhancers typically function to modify structure especially of the stratum corneum by dissolving or interfering with the lipid matrix to improve permeability of drug compounds. Examples include compounds like capric acid, oleic acid, azone, decylmethyl sulfoxide and hydroxy cinnamates. Dermal absorption of progesterone for example increases by 143% when the stratum corneum is delipidized. The enhancement increases to 843% when the stratum corneum is totally eliminated. With such aggressive modification, commonly reported problems with repeated use of such systems include contact dermatitis, reddening of the skin, itching and burning that requires movement of the patch or application of the drug, around the body to prevent local irritation. The reddening is said to disappear within hours of removing the patch. But concern has been raised with respect to long term risk and safety of use of this type of transdermal delivery system, mainly because increased drug permeability is achieved at the cost of damaging a fundamentally important protective layer of the skin.

A study by Morgan, T M. et al (1998). "Enhanced transdermal delivery of sex hormones in swine with a novel topical aerosol" *J Pharm. Sci.* 87(10): 1219-1225 investigated the transdermal delivery of testosterone and estradiol in pigs using a novel metered dose topical aerosol containing a penetration enhancer padimate O. The authors claim that the dose system provides flexibility and can be moved around to provide a greater surface area of application. However, metered dose devices require co-ordination and manual dexterity for efficient use.

There have been a number of attempts to develop drug delivery systems which are less aggressive to the skin, however none of these attempts have provided commercially acceptable products. For example:

U.S. Pat. No. 6,479,540 discloses use of a tocol based delivery system to solublize charged amphophilic and water soluble pharmaceutically active compounds. The patent teaches that the charged esters of tocopherol, such as phosphate, succinate, aspartate and glutamate form ion pairs with suitable drug substrates which in turn associate with the tocol emulsion. The formulation thus renders the active compound to be much more lipophilic and incorporated in miscelles that may permit better transport through mucosal membranes.

U.S. Pat. No. 5,583,105 discloses use of tocol and tocol derivatives including tocopherol polyethylene glycol 1000 succinate (TPGS) as solvents to dissolve certain drugs at high enough concentrations to be therapeutically useful. Emulsions and emulsification with solublizers have a long history in drug delivery art. TPGS is used as a pharmaceutically acceptable water miscible solubilizer and there is no teaching regarding any other interaction between TPGS with lipophilic pharmaceuticals.

International patent application WO 96/21440 discloses a method for improving bioavailability of a medicinal agent by covalent attachment of inositol phosphate and biphosphonate molecules. The resulting conjugates are said to have increased water solubility relative to the unconjugated agent.

The art of efficient topical drug delivery therefore requires that the drug be both soluble in the aqueous biological medium and in an appropriate form to permit transport of either individual drug molecules or very small aggregates of the drug molecules. This aim may be difficult to realise with drugs that are lipid soluble and not significantly water soluble, unless the delivery system is recognised by normal membrane transport systems. Such drug molecules have hydrophobic regions that form large aggregates in the high dielectric constant water rich medium where transport occurs.

A suitable carrier capable of topically delivering a broad range of pharmaceuticals or pharmacologically active compounds and improving absorption of the pharmaceutical or pharmacologically active compound in the targeted area without damaging the skin is therefore required.

SUMMARY OF THE INVENTION

It has surprisingly been found that a carrier composition comprising complexes of phosphates of lipophilic pharmaceutically acceptable compounds, such as tocopheryl phosphate, mixed with pharmaceuticals or their phosphorylated analogue allows rapid and efficient transport of the pharmaceuticals or pharmacologically active compounds.

When applied topically, the pharmaceutical is absorbed through the skin with no evidence of inflammation or disruption. This carrier can be used for therapies that require chronic administration and where the carrier needs to have reduced side effects and improve the well being of the patient.

Many lipophilic phosphates are known to be important in cellular function and are efficiently transported in the body. These transport mechanisms appear to tolerate substances which are associated with the lipophilic phosphates, so making this groups of compounds uniquely valuable as enhancers.

According to the first aspect of the invention, there is provided a carrier for use in topical administration of pharmaceuticals and pharmacologically active compounds, said carrier comprising an effective amount of one or more complexes of a phosphate derivative of a lipophilic pharmaceutically acceptable compound.

Preferably, the complex of a phosphate derivative of a lipophilic pharmaceutically acceptable compound is selected from the group comprising one or more complexes of phosphate derivatives of tocopherol.

According to a second aspect of the invention, there is provided a method for improving the efficacy and transdermal transport of topically administered pharmaceuticals and pharmacologically active compounds, said method comprising the step of incorporating the pharmaceutical or pharmacologically active compound in a carrier comprising an effective amount of one or more complexes of a phosphate derivative of a lipophilic pharmaceutically acceptable compound.

Preferably, the complex of a phosphate derivative of a lipophilic pharmaceutically acceptable compound is selected from the group comprising one or more complexes of phosphate derivatives of tocopherol.

The present invention also provides use of an effective amount of one or more complexes of phosphate derivatives of lipophilic pharmaceutically acceptable compounds, such as complexes of phosphate derivatives of tocopherol, together with other excipients in the manufacture of a carrier for use in the topical administration of pharmaceuticals or pharmacologically active compounds.

The present invention also provides a pharmaceutical composition comprising one or more pharmaceuticals or pharmacologically active compounds and a carrier comprising an effective amount of one or more complexes of phosphate derivatives of lipophilic pharmaceutically acceptable compounds, such as complexes of phosphate derivatives of tocopherol.

According to a further aspect of the invention, there is provided a method for improving the efficacy and transdermal transport of topically administered pharmaceuticals and pharmacologically active compounds, said method comprising the step of incorporating the pharmaceutical or pharmacologically active compound in a carrier comprising an effective amount of one or more phosphate derivatives of a lipophilic pharmaceutically acceptable compound.

This aspect of the invention includes a carrier for use in topical administration of pharmaceuticals and pharmacologically active compounds, said carrier comprising an effective amount of one or more phosphate derivatives of a lipophilic pharmaceutically acceptable compound.

The term "carrier" is used herein to refer to any formulation used in administration of a pharmaceutical topically on human or other animal skin to achieve a systemic or dermal effect. It includes but is not limited to creams, lotions, gels, emulsions, liposomes, aerosols, patches, poultices, subcutaneous depots, plasters and sustained release systems designed to alter absorption kinetics in favor of zero order release.

The term "effective amount" is used herein to refer to an amount of the one or more complexes of a phosphate derivative of a lipophilic pharmaceutically acceptable compound that enables the pharmaceutical or pharmacologically active compound to penetrate the stratum corneum to reach the epidermal and dermal layers of the skin in an amount that is measurably effective in the reduction of one or more symptoms presented by a patient. The effective amount of the one or more complexes of a phosphate derivative of a lipophilic pharmaceutically acceptable compound may range up to 99.99% w/w of the total weight of the carrier. A person skilled in the art will understand that the actual amount will vary from drug to drug. The effective amount will be sufficient to provide an amount within the therapeutic range of a drug. The amount used will also depend on whether the one or more complexes of a phosphate derivative of a lipophilic pharmaceutically acceptable compound are being used to assist with formulation properties, for example, solubilisation or surface activity. Where the one or more complexes of a phosphate of a lipophilic pharmaceutically acceptable compound is acting as a solubiliser, the effective amount will depend on the concentration of the drug in the formulation and may range from 40% to 90% w/w, preferably 45 to 75% w/w, more preferably 50 to 60% w/w. Where the one or more complexes of a phosphate of a lipophilic pharmaceutically acceptable compound is not required for solubilisation properties, the effective amount may be in the range of 0.01 to 20% w/w, preferably 1 to 15% w/w and more preferably 5 to 10% w/w.

Preferably (when solubilisation properties are not required), the effective amount of the one or more complexes of phosphate derivatives of tocopherol is in the range of from 0.1 to 10 % w/w of the total weight of the carrier. More preferably, in the range of 5 to 10% and most preferably 7.5% w/w.

The term "lipophilic pharmaceutically acceptable compound" refers to a compound which is uncharged and unable to readily form hydrogen bonds and thus the compound may be readily incorporated into a lipid phase, capable of phosphorylation (the phosphate group will be hydrophilic making the compound surface active) and is acceptable for use in pharmaceutical compounds or promotes absorption of a pharmaceutical compound.

Examples of such compounds include tocopherol (vitamin E), retinol (vitamin A), menadione (vitamin K), tocotrienols and calciferol (vitamin D). Based on our results from tests with complexes of tocopheryl phospates, we expect that similar results may be achieved with phosphate derivatives of other lipophilic pharmaceutically acceptable compounds. This expectation is based on the fact that lipophilic phosphate compounds are known to be important in cellular function and are efficiently transported in the body. Without wishing to be bound by theory it is believed that these lipophilic phosphate compounds function to support transport mechanisms in the skin and are thus uniquely valuable as enhancers.

The "phosphate derivatives of lipophilic pharmaceutically acceptable compounds" comprise compounds covalently bound by means of an oxygen to the phosphorus atom of a phosphate group thus forming a carbon-oxygen-phosphorous bond. The oxygen atom is typically derived from a hydroxyl group on the lipophilic pharmaceutically acceptable compounds. The phosphate derivative may exist in the form of a free phosphate acid; a salt thereof; a phosphate ester having two molecules of lipophilic pharmaceutically acceptable compounds or a phosphatidyl compound wherein the free phosphate oxygen forms a bond with an alkyl or substituted alkyl group.

The term "complexes of phosphate derivatives of lipophilic compounds" refers to the reaction product of one or more phosphate derivatives of the lipophilic compound and one or more complexing agents selected from the group consisting of amphoteric surfactants, cationic surfactants, amino acids having nitrogen functional groups and proteins rich in these amino acids as disclosed in international patent application no PCT/AU01/01476.

Preferably, the complexes of phosphate derivatives of tocopherol is prepared from a mixture of one mono-tocopheryl phosphate derivative and one di-tocopheryl phosphate derivative wherein the amount of mono-tocopheryl phosphate derivative is no less than equimolar to the amount of di-tocopheryl phosphate derivative as disclosed in international patent application no PCT/AU01/01475. For example, a mixture containing 70% tocopheryl phosphate and 26% di-tocopheryl phosphate.

The preferred complexing agents are selected from the group consisting of arginine, lysine and tertiary substituted amines, such as those according to the following formula:

$$NR^1R^2R^3$$

wherein $R^1$ is chosen from the group comprising straight or branched chain mixed alkyl radicals from C6 to C22 and carbonyl derivatives thereof;

$R^2$ and $R^3$ are chosen independently from the group comprising H, $CH_2COOX$, $CH_2CHOHCH_2SO_3X$, $CH_2CHOHCH_2OPO_3X$, $CH_2CH_2COOX$, $CH_2COOX$, $CH_2CH_2CHOHCH_2SO_3X$ or $CH_2CH_2CHOHCH_2OPO_3X$ and X is H, Na, K or alkanolamine provided $R^2$ and $R^3$ are not both H; and wherein when $R^1$ is R(CO) then $R^2$ may be $CH_3$ and $R^3$ may be $(CH_2CH_2)N(C_2H_4OH)$—$H_2CHOPO_3$ or $R^2$ and $R^3$ together may be $N(CH_2)_2N(C_2H_4OH)CH_2COO$—.

Preferably, the one or more complexes of phosphate derivatives of tocopherol is selected from the group consisting of laurylaminodipropionic acid tocopheryl monophosphate, laurylaminodipropionic acid tocopheryl diphosphate and mixtures thereof.

The term "pharmaceutical or pharmacologically active compound" is used herein to refer to pharmaceutically active compounds for human or veterinary application. Examples of pharmaceutical compounds include but are not limited to narcotic analgesics such as morphine and levorphanol, non narcotic analgesics such as codeine and acetaminophen, corticosteroids such as cortisone, anaesthetics such as propofol, antiemetics such scopolamine, sympathomimetic drugs such as adrenaline and dopamine, antiepileptic drugs such as fosphenytoin, anti-inflammatory drugs such as ibuprofen, thyroid hormones and antithyroid drugs including thyroxine, phytochemicals including α-bisabolol, eugenol, silybin, soy isoflavones, iridoid gylcosides including aucubin and catalpol, sesquiterpene lactones including pseudoguaianolide from *Arnica chamissonis*, terpenes including rosmarinic acid and rosmanol, phenolic glycosides including the salicylates salicin, saligenin and salicydic acid, triterpenes taxasterol or α-lactucerol, and isolactucerol, p-hydroxyphenylacetic acid derivative taraxacoside, hydroquinone derivatives including arbutin, phenylalkanones including gingerols and shagaols, hypercin, and acylphloroglucides including xanthohumol, lupulone, humulone and 2-methylbut-3-en-2-ol. The pharmaceutical or pharmacologically active compound can be in any suitable form including phosphate derivatives.

A person skilled in the art would know which other excipients could be included in the carrier. The choice of other excipients would depend on the characteristics of the pharmaceutical or pharmacologically active compound. Examples of other excipients include solvents, surfactants, emollients, preservatives, colorants, fragrances and the like. The choice of other excipients will also depend on the form of topical administration used.

Typical excipients for a carrier according to the invention comprises 61.95% deionized water, 5.00% glycerin, 0.05% trisodium EDTA, 0.50% carbomer (Carbopol Ultrez 10), 2.00% Phoenoxol T (cetearyl alcohol and ceteareth-20), 1.00% glyceryl stearate (Emerest 2400), 5.00% isopropyl myristate (Pelemol IPM), 3.50% cetyl ethylhexanoate (Pelemol 168), 3.50% isocetyl behenate (Pelemol ICB), 3.00% oleyl erucate (Cetiol J-600), 0.50% dimethicone (Dow 200,100 cSt.), 5.00% deionized water, 0.50% triethanolamine (99%) and 1.00% Germaben II (propylene glycol, diazolidinyl urea, methylparaben and propylparaben).

EXAMPLES

Figure 1:
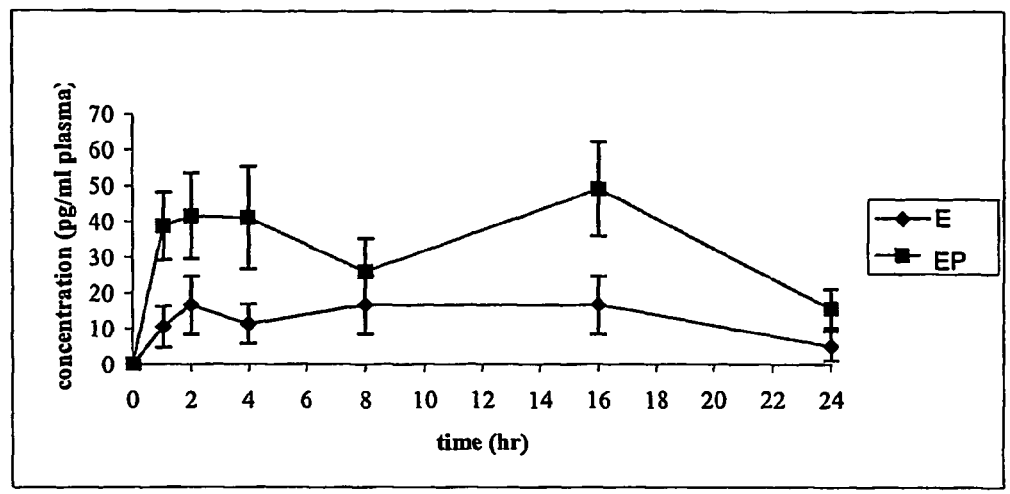
FIG. 1: Changes in total estrogens (mean±SE) measured in plasma samples obtained from ovariectomised hairless rats to which formulations containing approximately 0.17 μg of estrogen (E) or estrogen phosphate (EP) were applied.
Figure 2:
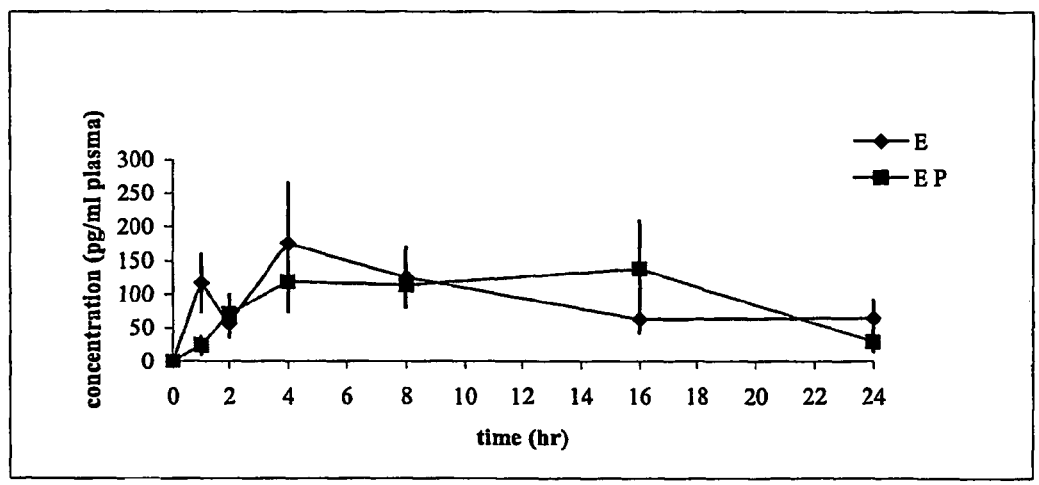
FIG. 2: Changes in total estrogens (mean±SE) measured in plasma samples obtained from ovariectomised hairless rats to which formulations containing approximately 0.17 μg of E or EP in ethanol were applied.

The invention is further explained and illustrated by the following non-limiting examples.

Example 1

A carrier cream according to the invention was prepared as follows:

|  | W/W |
|---|---|
| PHASE A | |
| Deionized water | 61.95% |
| Glycerin | 5.00 |
| Trisodium EDTA | 0.05 |
| Carbomer (Carbopol Ultrez 10)[2] | 0.50 |
| laurylaminodipropionic acid tocopheryl phosphate[1] | 7.50 |
| PHASE B | |
| Cetearyl Alcohol (and) Ceteareth-20 (Phoenoxol T)[3] | 2.00 |
| Glyceryl Stearate (Emerest 2400)[4] | 1.00 |
| Isopropyl Myristate (Pelemol IPM)[3] | 5.00 |
| Cetyl Ethylhexanoate (Pelemol 168)[3] | 3.50 |
| Isocetyl Behenate (Pelemol ICB)[3] | 3.50 |
| Oleyl Erucate (Cetiol J-600)[4] | 3.00 |
| Dimethicone (Dow 200, 100 cSt.)[5] | 0.50 |
| PHASE C | |
| Deionized Water | 5.00 |
| Triethanolamine (99%) | 0.50 |
| PHASE D | |
| Propylene Glycol (and) Diazolidinyl Urea (and) Methylparaben (and) Propylparaben (Germaben II)[6] | 1.00 |

[1]Vital Health Sciences Pty Ltd
[2]B. F. Goodrich, Incorporated
[3]Phoenix Chemical, Incorporated
[4]Cognis, Incorporated
[5]Dow-Corning, Incorporated
[6]ISP Corporation Procedure:

Procedure: Combine Phase A items minus the Carbomer and laurylaminodipropionic acid tocopheryl phosphate with stirring. When a solution is obtained, disperse Carbomer in this solution. Begin heating Phase A to 70-75° C. with adequate agitation. Disperse laurylaminodipropionic acid tocopheryl phosphate in Carbomer mucilage with sweep agitation. Combine Phase B items and heat to 75-80° C. with adequate agitation with Phase A uniform and at 70-75° C. and Phase B uniform and at 75-80° C. Add Phase B to Phase A with adequate agitation. Allow AB to cool to 50° C. and then add Phase C solution to AB. Continue adequate agitation of ABC until 45° C. is reached. Add Phase D to ABC. Continue adequate agitation until 35° C. is reached.

Example 2

The transdermal delivery of estradiol and estradiol 3:phosphate in the hairless rat model was evaluated in this example.

Methods

Animals: 23 female albino hairless rats were ovariectomised under isoflurane-induced anaesthesia and allowed to recover for 10 days prior to experimentation. This should allow clearance of any estrogens from the body.

Blood sampling: Blood samples (500 μl) were obtained from the tail vein of conscious restrained rats at 0, 1, 2, 4, 8, 16 and 24 hours following application of both the estradiol (n=5) and estradiol phosphate (n=6) formulations. Blood was collected into EDTA tubes, then centrifuged at 5000 rpm for 10 minutes. Plasma was removed and stored at −80° C. until assayed.

Transdermal Formulation Preparation and Application: estradiol and estradiol phosphate were provided by Vital Health Sciences Pty Ltd and prepared at concentrations of 20 µg/ml approximately 1 hour before application in the carrier cream from Example 1.

Estradiol Phosphate (EP): 4.3 mg of EP was dissolved in 17.3 ml of acetone (0.25 mg/ml). 20 µl was transferred to an Eppendorf tube and the solvent was evaporated in a nitrogen stream. Then 0.999 g of the carrier cream from example 1 was added, and mixed with a glass rod and centrifuged. This was repeated 5 times. Final concentration=4.90 µg/ml.

Estradiol (E): 6.7 mg was dissolved in 26.8 ml of absolute ethanol (0.25 mg/ml). 20 µl was transferred to an Eppendorf tube and the solvent was evaporated in a nitrogen stream. Then 1.003 g of the carrier cream from example 1 was added, and mixed with a glass rod and centrifuged. This was repeated 5 times. Final concentration=4.89 µg/ml.

E and EP formulations in ethanol: 0.5 mg of E and EP was mixed with 50 ml portions of ethanol. 20 µl of these solutions was directly applied to the skin.

Each formulation was applied to the dorsal skin of an anaesthetised rat in an area of approximately 4 $cm^2$ marked with an indelible felt tip marker. Application of approximately 30±3.2 mg of formulation (containg 0.15±0.02 µg of E or EP) was applied to the site with a curved glass rod applicator. The formulation was 'rubbed' in until it appeared to have been absorbed into the skin, which took between 5-10 min. Any changes in the consistency of the formulation during this procedure were noted The amount of formulation applied and the area of the application site were weighed for each animal.

Organ Collection: After 24 hr monitoring animals were killed with an overdose of anaesthetic. All organs were removed, weighed and stored at −80° C. until assay.

Total Estrogens RIA: The RIAs were performed using a commercially available total estrogens kit (ICN Pharmaceuticals, catalogue #07-140205) with 100% cross-reactivities for 17β-estradiol and estrone. The standard curve range for this assay is 2.5-100 pg/ml ($r^2$=−0.943). Extraction efficiency was determined through a series of spiking assays and was between 90 to 98% using diethyl ether as the extraction solvent for rat plasma and organs. This solvent did not interfere with the assay. Plasma volumes of 100 µl were used for assay.

Results

Formulation Application: The average areas (±SE) to which formulations were applied on the dorsum of the animals were 3.88±0.03 $cm^2$ and 3.88±0.07 $cm^2$ for the E and EP groups respectively. The average amounts of these formulations applied in the E and EP groups were 0.15±0.02 µg. No symptoms of inflammation were observed in the study such as erythema or oedema.

Total Estrogens in Plasma: Measurable levels of estrogens (between the standard curve range of 2.5-100 pg/ml) were present in both groups of animals with maximum concentrations of 16.63±8.18 (mean±SE) pg/ml plasma measured in the E group at 2, 8 and 16 hr post-application and a maximum concentration of 49.16±13.21 pg/ml plasma measured at 16 hr post-application in the EP group (FIG. 1). Baseline measurements taken at t=0 were subtracted from all values to correct for background levels present in the plasma.

Discussion

This study evaluated the transdermal delivery of EP and E in female hairless rats. The concentration of estradiol in blood was consistently higher when estradiol phosphate was applied over a 24 hour period (statistically significant, P<0.01 at 2, 4 and 16 hours). At the equivalent doses that were applied the EP resulted in at least twice the plasma concentration of the hormone compared to the E treatment. This clearly demonstrates that EP delivered in the carrier from example 1 may provide a more effective formulation for delivering E. Interestingly the amount of free estradiol delivered after application of E in the carrier from example 1 was also quite significant. Most importantly, neither E or EP treatment produced any inflammatory symptoms.

Morgan et al. (Morgan T M, O'Sullivan H M M, Reed B L, Finnin B C. Transdermal Delivery of Estradiol in Postmenopausal Women with a Novel Topical Aerosol. *J. Pharm. Sci.* 1998; 87(10):1226-1128) delivered 3 mg of estradiol daily a carrier containing the skin enhancer padimate O containing over 30 $cm^2$ in 4 post menopausal women for 9 days. At the end of the study period mean blood levels of estradiol 24 hours post dose were 53±7 pg/ml measured with commercial radio immunoassay kits measuring both estradiol and estrone. This was said a significant 4 fold improvement from a baseline level of circulating estradiol of 13±5 pg/ml and deemed to be a clinically relevant dose.

In contrast, in this example maximum plasma concentrations of 16.63±8.18 (mean±SE) pg/ml were detected in the E group at 16 hr post-application and a maximum concentration of 49.16±13.21 pg/ml at the same time point in the EP group (FIG. 1) following 0.17 µg applied over an average surface area on the dorsum of the animals of 3.88±0.03 $cm^2$ and 3.88±0.07 $cm^2$ for the E and EP groups respectively. Ignoring the differences in skin physiology between the animal model and human skin, approximately the same estradiol levels were achieved even though substantially smaller doses were used in the compositions containing a carrier according to the invention.

Although different models were used, comparisons with other studies reveal that the carrier according to the invention stimulated transport of estradiol through the skin.

Conclusion

The trial demonstrated that useful doses of estradiol may be delivered based on the hairless rat model and it may be inferred from the similarity of the properties of the hairless rat to human skin, that estradiol phosphate formulated in the manner proposed in this invention, may prove to be efficacious for hormone replacement therapy. Interestingly the extremely low drug doses utilised in this example managed to deliver potentially therapeutic doses of estradiol. It is quite clear that the carrier was able to release significant amounts of free estradiol into the blood and is therefore likely to promote the required biological response at the site of action.

The trial also demonstrated that the carrier utilised in both treatment arms not only improved the absorption of estradiol phosphate but of estradiol. This suggests that carrier dependant stimulation of absorption was independent of the drug analogue used.

Without wishing to be bound by theory, the significant improvement of transport appears to be due to the benign interaction of the carrier according to the invention with the lipids in the stratum corneum and may be related to the unique surfaction system of the carrier of this invention.

Consistent with previously published literature on ethanol formulations, greater amounts of estradiol are delivered through the skin which is probably due to cellular disruption caused by the stripping of the stratum corneum. However, following application of the ethanol formulation, skin irritation, erythema and damage was observed. There was no irritation of the skin when the carrier from Example 1 was used.

Example 3

The acute transdermal penetration of $^3$H-Estradiol ($^3$H-E) and $^3$H-Estradiol Phosphate ($^3$H-EP) in the hairless rat model was evaluated in this example.

Methods

Animals: 6 female albino hairless rats were used in this study (n=3 per treatment group).

Transdermal Formulation Preparation and Application: $^3$H-E and $^3$H-EP were provided by Vital Health Sciences Pty Ltd and prepared in formula approximately 1 hour before application in in the carrier cream from Example 1.

20 µl of $^3$H-E and $^3$H-EP were aliquoted into 1 ml Eppendorf tubes. The solvents from both $^3$H-E and $^3$H-EP were evaporated under a stream of nitrogen. Once completely dry 0.498 g of the carrier cream of example 1 was added to $^3$H-E and 0.502 g to $^3$H-EP and mixed with a glass rod and centrifuged for 1 minute. This was repeated 5 times.

Each formulation was applied to the dorsal skin of an anaesthetised rat in an area of approximately 4 cm$^2$ marked with an indelible felt tip marker. Application of approximately 30 mg of formulation (containing 5 µg of $^3$H-E and $^3$H-EP) was applied to the site with a curved glass rod applicator. The formulation was 'rubbed' in until it appeared to have been absorbed into the skin, which took between 5 to 10 minutes. A tegaderm (3M) patch was applied to the area to prevent animals from removing the formulation.

Results and Discussion

Figure 3:
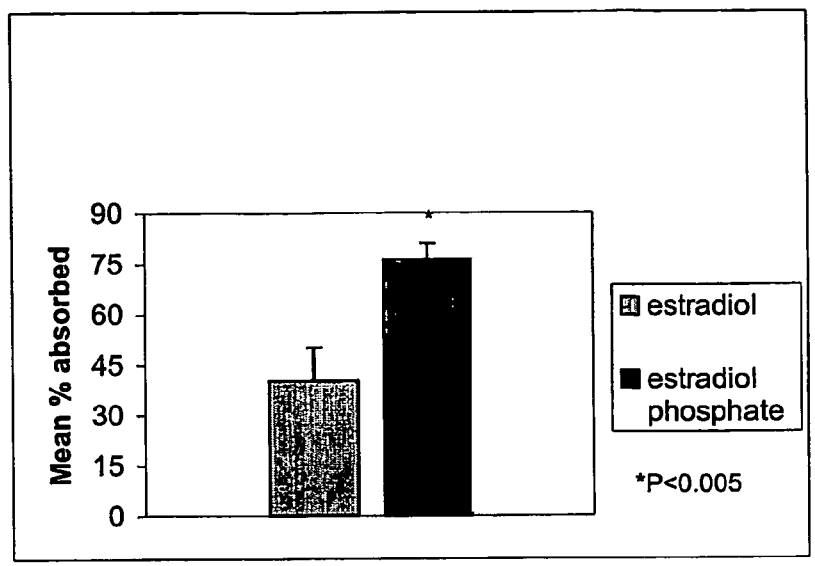
FIG. 3: Percent absorption of tritiated E vs tritiated EP in ovariectomised hairless rats 24 hours after formulations containing tritiated E or EP were applied.
Figure 4:
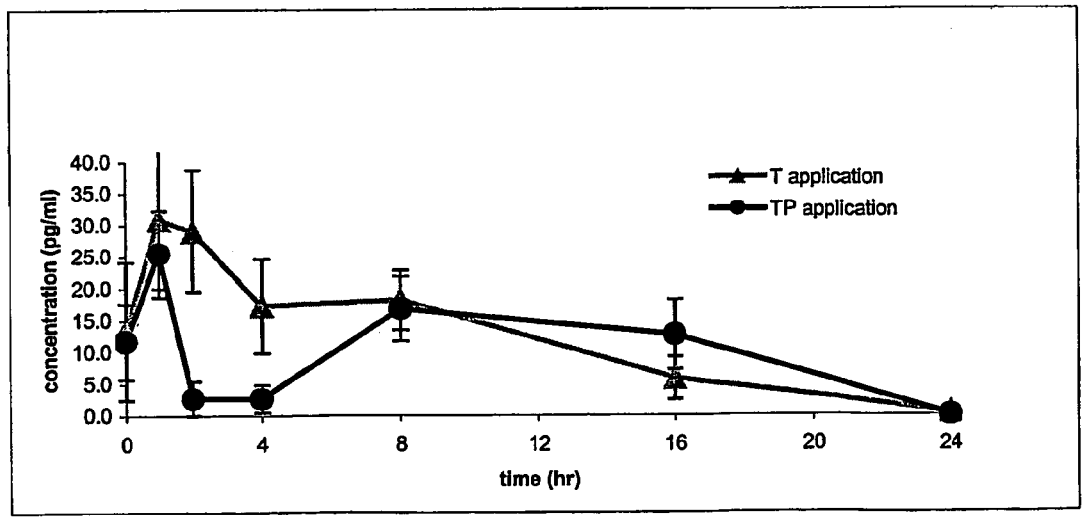
FIG. 4: Changes in total testosterone (mean±SD) measured in plasma samples obtained from ovariectomised hairless rats to which formulations containing approximately 1.00 μg±0.02 μg of T or TP were applied.

This study dearly demonstrates that EP was more readily absorbed in comparison to E when transdermally applied using the invention (FIG. 3). While the drug form had a significant impact on improving the amount of estradiol delivered it is important to note that the carrier stimulated rapid transport of both drug analogues through the skin. Analysis of individual skin layers was also undertaken in this study and revealed that minimal E or EP remained in the skin 24 hours after application. Higher levels of EP were found in the epidermis and dermis due to higher volumes of the EP moving through the skin during the 24 hour period.

Conclusion

The trial demonstrated that useful doses of estradiol may be delivered based on the hairless rat model. It is quite dear that the carrier was able to release significant amounts of free estradiol into the blood and is therefore likely to promote the required biological response at the site of action.

The trial also demonstrated that the carrier utilised in both treatment arms not only improved the absorption of estradiol phosphate but of estradiol. This suggests that carrier dependant stimulation of absorption was independent of the drug analogue used.

Example 4

The transdermal delivery of testosterone and testosterone phosphate in the hairless rat model using the carrier from Example 1 was investigated in this example.

Methods

Animals: 12 Female albino hairless rats were ovariectomised under isoflurane-induced anesthesia and allowed to recover for 15 days prior to experimentation.

Blood Sampling: Blood samples (500 µl) were obtained from the tail vein of conscious restrained rats at 0, 1, 2, 4, 8, 16 and 24 hr following application of both testosterone (n=6) and testosterone phosphate (n=6) formulations. Blood was collected into EDTA tubes, then centrifuged at 5000 rpm for 10 min. Plasma was removed and stored at −80° C. until assay.

Transdermal Formulation Preparation and Application: Testosterone and testosterone phosphate were provided by Vital Health Sciences Pty Ltd and prepared in the carrier from Example 1 approximately 1 hour before application.

Testosterone Phosphate (TP): 4.41 mg of TP was dissolved in 15 ml of water and then made up to 100 ml with ethanol. 1 ml was transferred to an Eppendorf tube and the solvent was evaporated under a nitrogen stream. 1.00 g of the carrier from Example 1 was added and mixed with a glass rod and centrifuged. This was repeated 5 times.

Testosterone (T): 3.94 mg of T was dissolved in 15 ml of water and then made up to 100 ml with ethanol. 1 ml was transferred to an Eppendorf tube and the solvent was evaporated under a nitrogen stream. 1.00 g of the carrier from Example 1 was added and mixed with a glass rod and centrifuged. This was repeated 5 times.

Each formulation was applied to the dorsal skin of an anaesthetized rat in an area of approximately 4 cm$^2$ marked with an indelible felt tip marker. Application of approximately 30 mg of formulation (containing 1 µg of T or TP) was applied to the site with a curved glass rod applicator. The formulation was 'rubbed' in until it appeared to have been absorbed into the skin, which took between 5 to 10 min. Any changes in the consistency of the formulation during this procedure were noted.

Results

Formulation Application: The average amounts of these formulations applied in the T and TP groups were 1 µg±0.02 µg.

Total Testosterone in Plasma: Measurable levels of testosterone (between standard curve range 2.5-100 pg/ml) were present in both groups of animals with maximum concentrations of 30.90±11.00 (mean±SD) pg/ml plasma measured in the T groups at 1, 8 and 16 hr post-application. Baseline measurements were taken at t=0 and these values were subtracted from all values to correct for background levels in the plasma.

Normal levels of testosterone for males is 437 to 707 pg/ml and in females is 24 to 47 pg/ml. The 1 µg dose applied in this study may therefore provide a therapeutic dose in females.

Discussion

The concentration of testosterone in blood increased when both testosterone and testosterone phosphate was applied. This suggests that testosterone and testosterone phosphate formulated in the carrier from example 1 provides an effective formulation for delivering testosterone.

Example 5

The transdermal delivery of atropine in rats using the carrier from Example 1 was investigated in this example.

Intravenous (IV) Studies

Figure 5:
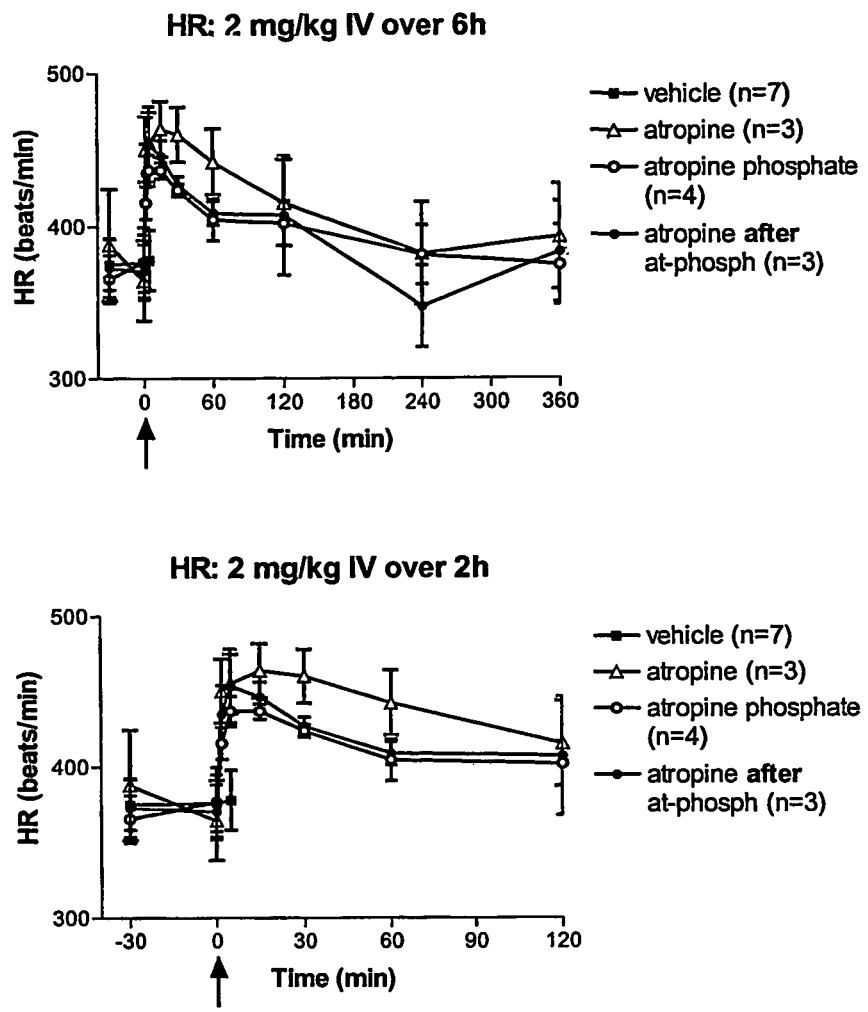
FIG. 5: Effect of atropine (2 mg/kg, IV) formulations on heart rate (HR) in conscious rats recorded over 6 hours (upper panel) and 2 hours (expanded view, lower panel). Arrow depicts time of drug administration.
Figure 6:
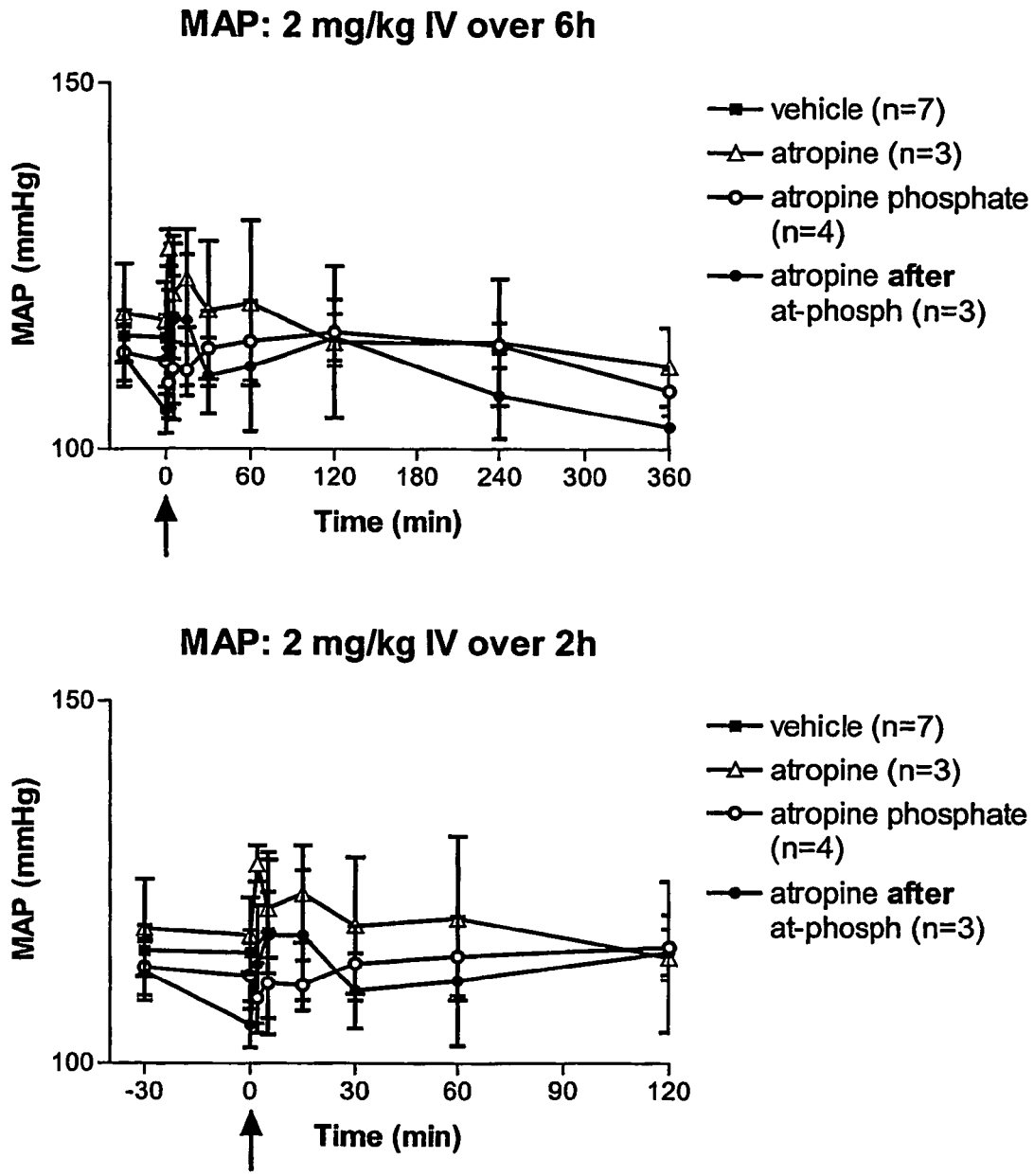
FIG. 6: Effect of atropine (2 mg/kg, IV) formulations on mean arterial pressure (MAP) in conscious rats recorded over 6 hours (upper panel) and 2 hours (expanded view, lower panel). Arrow depicts time of drug administration.

Conscious Sprague Dawley rats were given IV injections of either atropine sulphate (Sigma Catalogue #A-0257) (n=3) or atropine phosphate (n=4) at a dose of 2 mg/kg and monitored for 6 hours. Saline was given to all animals (n=7) prior to administration of either atropine formulation. Results are set out in FIGS. 5 and 6.

$P<0.05$ for first 60 min after administration versus pre-drug baseline, for atropine sulfate given to naive rats.

$P<0.05$ for first 30 min after administration versus pre-drug baseline, for atropine sulfate given to rats treated 24 hours previously with atropine phosphate.

P<0.05 for first 30 min after administration versus pre-drug baseline, for atropine phosphate given to naive rats.

Results:
  Saline (n=7) had negligible effect on heart rate (HR) and mean arterial pressure (MAP) over 5 min.
  Atropine sulfate (n=3) caused a significant increase in HR (1-way ANOVA with repeated measures, P<0.05) but not MAP, as expected. This effect lasted for approximately 60 min after injection.
  Atropine phosphate (n=4) caused a significant increase in HR (1-way ANOVA with repeated measures, P<0.05) but not MAP. This effect lasted for approximately 30 min after injection.
  Atropine sulfate was also given (on a subsequent day) to 3 out of 4 rats that had previously received (i.e. after) atropine phosphate. Atropine sulfate evoked a very similar time course of increased HR (1-way ANOVA with repeated measures, P<0.05) to that seen with atropine phosphate.

Transdermal Patch Studies

Figure 7:
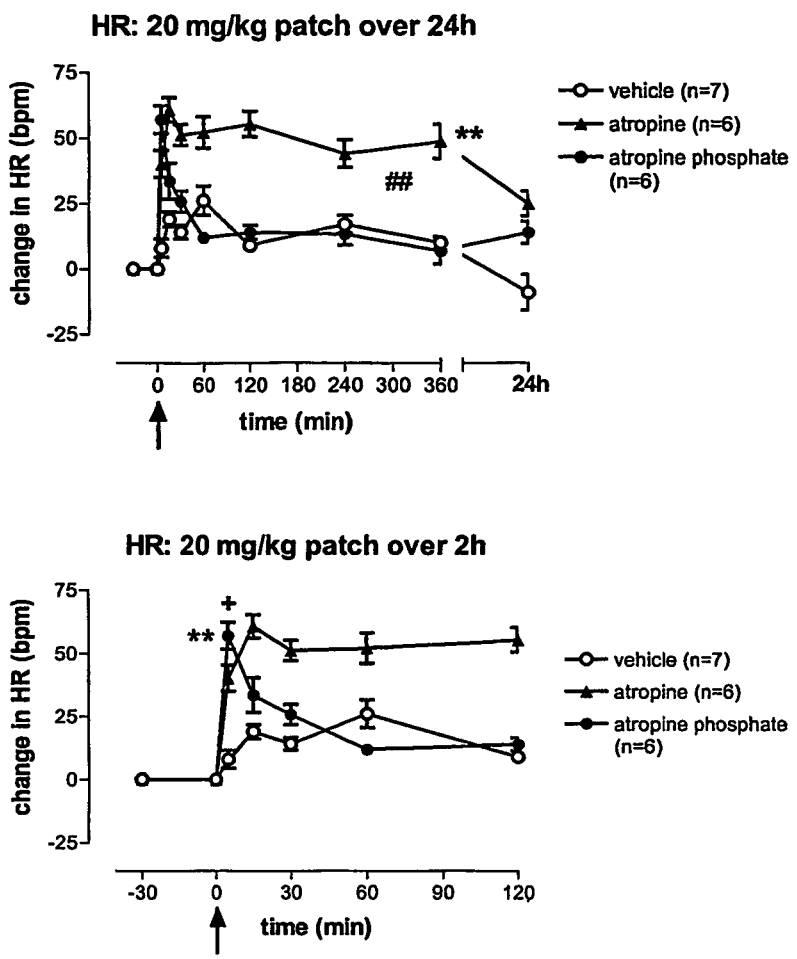
FIG. 7: Effect of atropine (20 mg/kg, topical) formulations on heart rate (HR) in conscious rats recorded over 24 hours (upper panel) and 2 hours (expanded view, lower panel). Arrow depicts time of drug administration.
Figure 8:
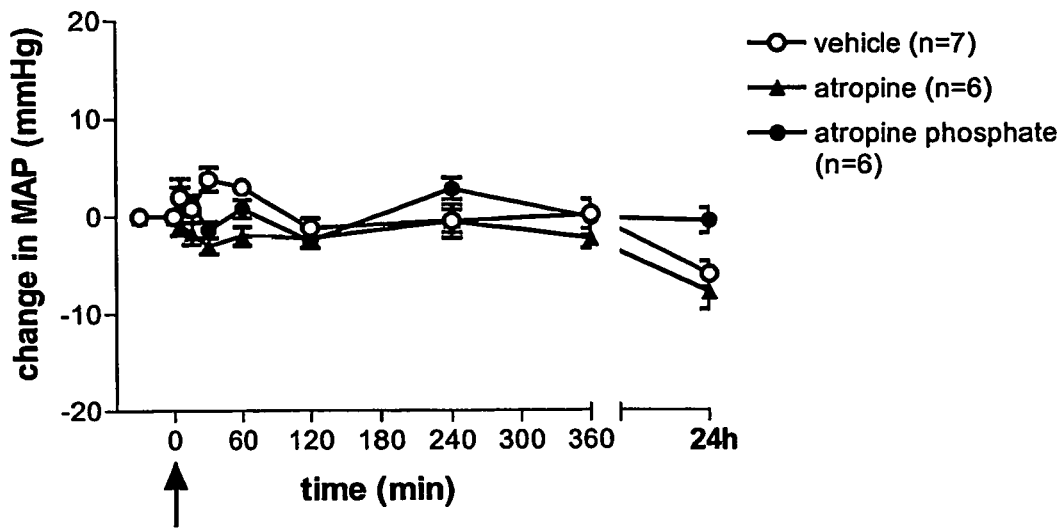
FIG. 8: Effect of atropine (20 mg/kg, topical) formulations on mean arterial pressure (MAP) in conscious rats recorded over 24 hours (upper panel) and 2 hours (expanded view, lower panel). Arrow depicts time of drug administration.
Figure 8:
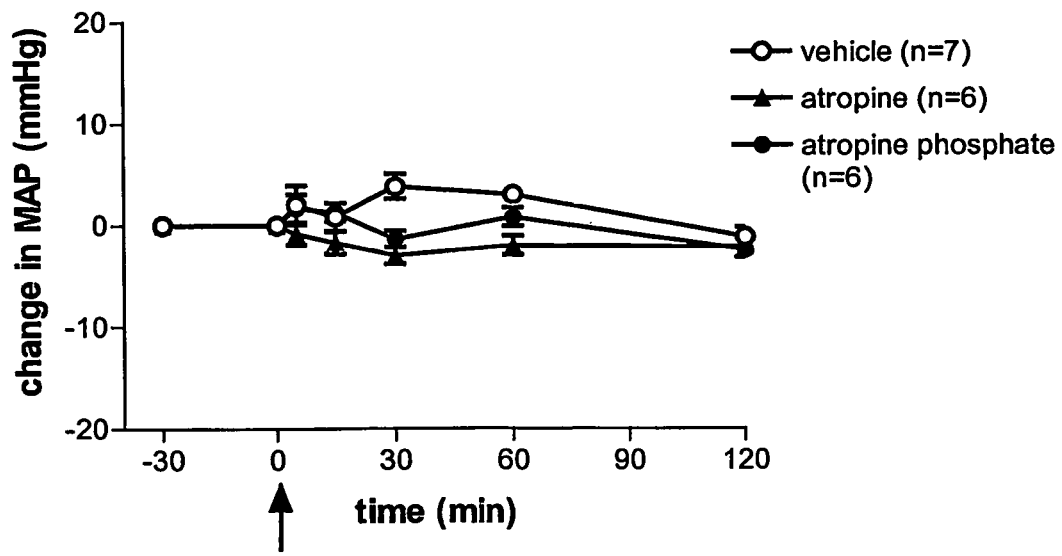

Conscious Sprague Dawley rats received atropine sulphate (formulated in the carrier according to Example 1 at 20 mg/kg, n=6) or atropine phosphate (formulated in the carrier according to example 1 at 20 mg/kg, n=6), which was topically applied to the dorsal hindquarter skin (that had been shaved and treated with 'hair-remover' 24 hours earlier). Skin area exposed to drug/vehicle was then covered with a Tegaderm (3M) patch and animals were monitored for 24 hours. Concious Sprague Dawley rats also received atropine sulphate 2 mg/kg by intravenous administration. Results are set out in FIGS. 7 and 8.

P<0.01 for 6 hours after atropine sulfate administration versus pre-drug baseline (1-way RM ANOVA).
P<0.01 for atropine sulfate effect versus vehicle (2-way RM ANOVA).
P<0.01 for 5 min after atropine phosphate administration versus pre-drug baseline (1-way RM ANOVA).
⁺P<0.05 for atropine phosphate treatment/time interaction versus vehicle (2-way RM ANOVA).

Results:
  The carrier according to Example 1 alone (n=7) had negligible effect on heart rate (HR) and mean arterial pressure (MAP) over 24 hour period
  Atropine sulfate caused a rapid and sustained increase in HR over 6 hours, in rats, which had recovered by 24 hours. This effect was significant versus its own pre-drug baseline and IV administered atropine sulphate (1-way ANOVA with repeated measures, P<0.01), as well as against the vehicle-treated group (2-way ANOVA with repeated measures, P<0.01). Atropine sulfate did not alter MAP.
  Atropine phosphate increased HR, but only at 5 min (P<0.01), and this tachycardia quickly waned. This effect was significant versus its own pre-drug baseline, as well as against the vehicle-treated group (2-way ANOVA with repeated measures, treatment/time interaction, P<0.01). Atropine phosphate did not alter MAP.

Conclusion

Atropine formulated in the carrier according to Example 1 caused statistically significant tachycardia when given by IV and topical administration (up to 6 hours). Atropine phosphate appeared to be similarly active to atropine following IV administration, but was less effective (refer to FIG. 3) following topical administration. Importantly, mean arterial blood pressure did not change significantly during the change in heart rate. This strongly indicates that the change in heart rate was due to effective transdermal delivery of atropine and not induced by handling of the laboratory animals or other experimental conditions.

Example 6

The transdermal delivery of morphine in rats using the carrier from Example 1 was investigated in this example.

Methods

Animals: Conscious Sprague Dawley Rats (~280 g) n=6 per group.

Transdermal Formulation Preparation: Morphine HCl, Glaxo Australia Pty Ltd (catalogue number 22284). Morphine free base was derived from HCL form in aqueous solution by the addition of potassium carbonate. This process was completed at Monash University. (Morphine HCl could not be used with creams, so free base was used).

Morphine (10 mg/kg) applied in the carrier from Example 1 and compared to the same dose given intraperitoneally. The effect was measured by the delayed response of the rat to heat with the delay in time taken to withdraw the pat taken as the action of morphine.

Intraperitoneal (i.p.) formulation: Morphine HCl, Glaxo Australia Pty Ltd (catalogue number 22284) dissolved in saline –3 and 10 mg/kg doses.

Test Method:

The plantar analgesiometer is designed for rapid and efficient screening of analgesia levels in small laboratory animals. The device is used to apply a heat source (~45° C. from an infrared light) to the animal's hindpaw and the time taken to withdraw the paw is measured (paw withdrawal latency). The hot plate provides a constant surface temperature, with a built-in digital thermometer with an accuracy of 0.1° C. and a timer with an accuracy of 0.1 second. The animal is placed on a hot plate, confined by a dear acrylic cage which surrounds the plate and paw-lick response is monitored. An increased time period before paw-lick response indicating analgesia.

Systemic Analgesic Studies

Conscious Sprague Dawley rats were tested in the analgesic test before and after an intraperitoneal (i.p.) injection of either saline or morphine hydrochloride (HCl) at 2 doses: 3 and 10 mg/kg to separate groups of rats.

Figure 9:
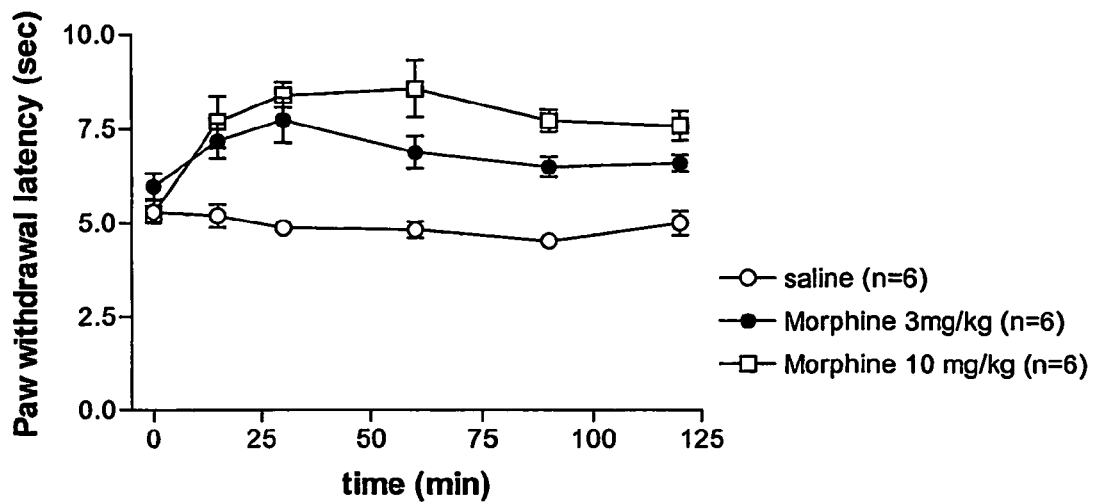
FIG. 9: Effect of morphine at 3 or 10 mg/kg intraperitoneal on paw withdrawal latency, tested over 2 hours.
Figure 10:
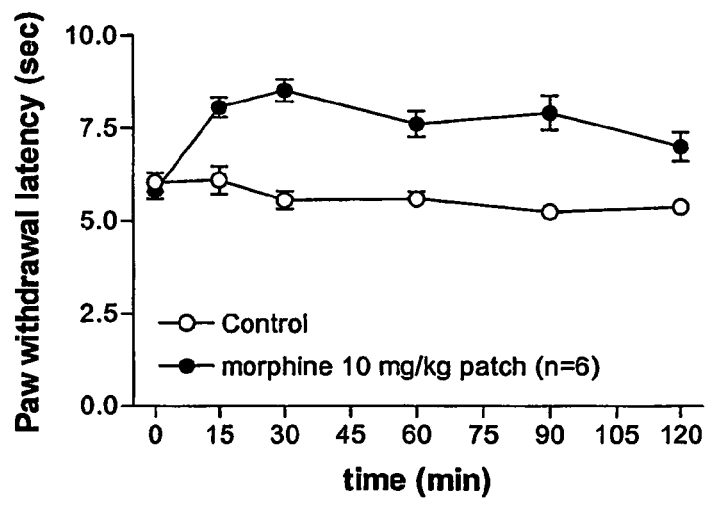
FIG. 10: Effect of morphine 10 mg/kg in carrier on paw withdrawal latency, tested over 2 hours (pooled data).
Figure 11:
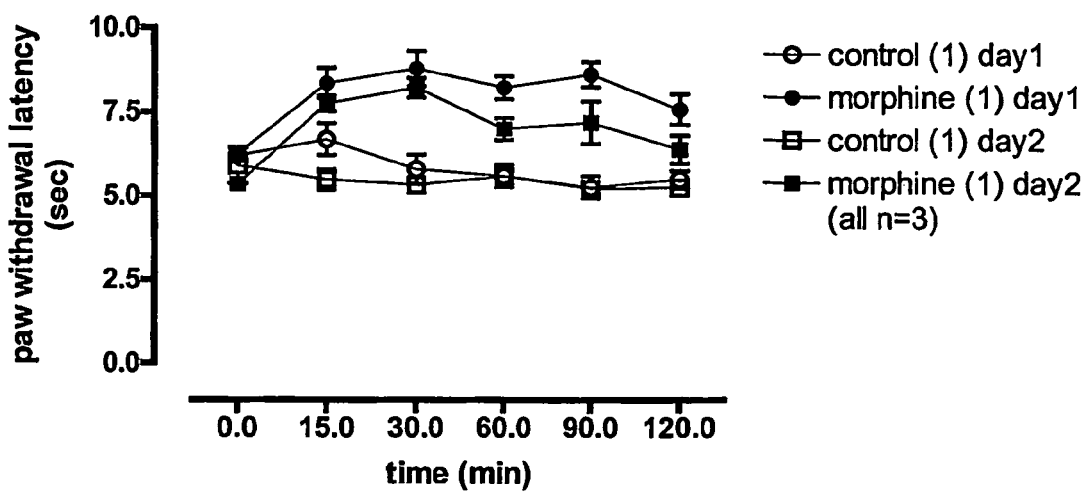
FIG. 11: Data from FIG. 2 plotted as a daily average for control vehide (each n=3) or morphine (each n=3)
Figure 12:
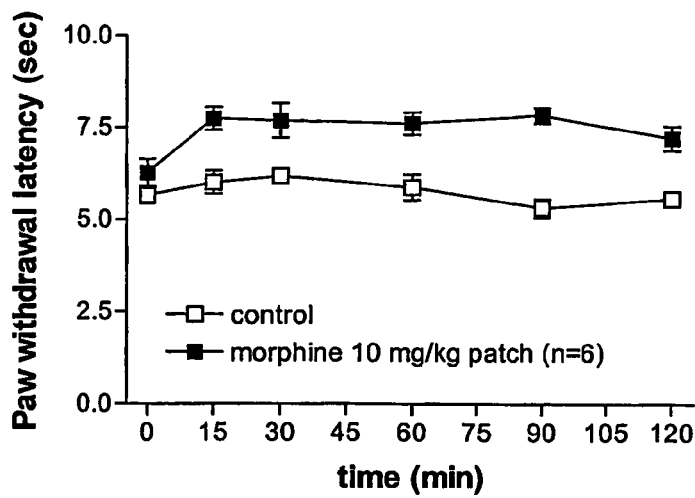
FIG. 12: Effect of morphine 10 mg/kg in carrier on paw withdrawal latency, tested over 2 hours (pooled data).
Figure 13:
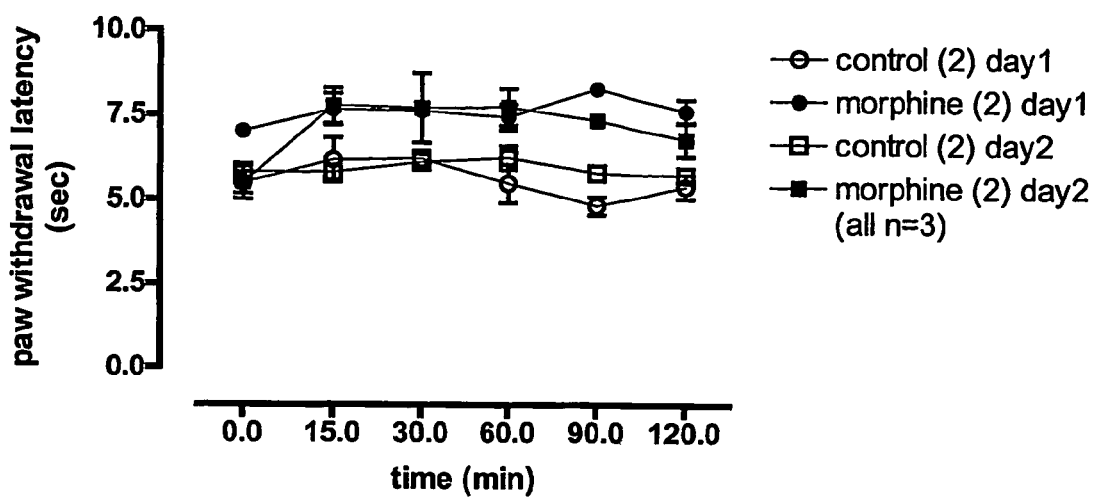
FIG. 13: Data from FIG. 4 plotted as a daily average for control vehide (each n=3) or morphine (each n=3)

The results are set out in FIG. 9. Saline (n=6) had no effect on latency. Morphine appeared to cause a dose-dependent increase in latency, indicating analgesia (positive control).

Transdermal Patch Studies

Rats had a hair removal cream applied to a dorsal hindquarter area of skin (under anaesthesia) at least 24 hours prior to any transdermal patch application. Conscious Sprague Dawley rats (~400 grams) received morphine at 10 mg/kg in the carrier from Example 1. This dose was chosen based on results in FIG. 9 of morphine HCl intraperitoneal injection. The skin area exposed to drug/vehicle was then covered with a Tegaderm patch. All animals underwent analgesic testing before and after morphine administration.

On the first test day, 3 animals received the carrier from Example 1 alone (vehicle) and 3 animals received morphine in the carrier from Example 1. On the following day, the treatments were reversed so that all 6 rats had been given either vehicle or morphine in a cross-over design over 2 days. The experiment was repeated on a second set of rats.

The results are set out in FIGS. 10 to 13. Carrier formulation alone (n=6) had no effect on paw withdrawal latency. Morphine in the carrier from Example 1 (n=6) increased paw withdrawal latency. Cross-over design showed similar results on either day 1 or day 2 (each n=3), indicating that morphine had no persistent effect after 24 hours because vehicle testing on day 2 (in the same rats after morphine testing on day 1) was similar to vehicle testing in other rats on day 1. However, on dose inspection of morphine data tested on day 1 (FIG. 12), this cohort of rats had a high baseline before administration of morphine, and this may have contributed to the relatively smaller increase in latency following morphine in this group.
Results:

The time-course of the responses is similar for all groups, that is, the effect of morphine was seen as early as 15 min after application. The maximum effects seem to be very similar in the groups, with similar delayed-response times between 15-90 min (i.e., plateaus in the effects between these times).

The rats' behaviour and appearance, once given the morphine treatment, was that of drowsiness and a slight slumping of the body, which are further indications of the magnitude of the effect of the morphine in the system when applied transdermally. This indicates that the drug was transferred through the skin and had some centrally mediated effects. There were no signs of erythema or irritation around the site of application.
Conclusion:

In conclusion, this data provides preliminary proof that morphine can be delivered through the skin using the carrier system according to the invention and mediates a central effect. In all cases, there were no signs of erythema or irritation associated with the areas of application.

Morphine in the carrier from Example 1 increased paw withdrawal latency, suggesting that analgesia had occurred following transdermal application of morphine.

The word 'comprising' and forms of the word 'comprising' as used in this description does not limit the invention claimed to exclude any variants or additions.

Modifications and improvements to the invention will be readily apparent to those skilled in the art. Such modifications and improvements are intended to be within the scope of this invention.

The claims defining the invention are as follows:

1. A method for improving the efficacy and/or transdermal transport of topically administered pharmaceuticals and pharmacologically active compounds, said method comprising the step of incorporating the pharmaceutical or pharmacologically active compound in a carrier comprising an effective amount of one or more complexes of a phosphorylated lipophilic pharmaceutically acceptable compound;
   from the group consisting of laurylaminodipropionic acid tocopheryl monophosphate, laurylaminodipropionic acid tocopheryl diphosphate, and mixtures thereof.

2. The method according to claim 1, wherein the effective amount of the one or more complexes of the phosphorylated lipophilic pharmaceutically acceptable compound is in the range from 1 to 90% w/w of the total weight of the carrier.

3. The method according to claim 2 wherein the effective amount is in the range from 40 to 90% w/w of the total weight of the carrier.

4. The method according to claim 3 wherein the effective amount is in the range from 45 to 75% w/w of the total weight of the carrier.

5. The method according to claim 4 wherein the effective amount is in the range from 50 to 60% w/w of the total weight of the carrier.

6. The method according to claim 2 wherein the effective amount is in the range from 1 to 15% w/w of the total weight of the carrier.

7. The method according to claim 2 wherein the effective amount is in the range from 1 to 10% w/w of the total weight of the carrier.

8. The method according to claim 7 wherein the effective amount is in the range from 5 to 10% w/w of the total weight of the carrier.

9. The method according to claim 1, wherein the carrier further comprises excipients selected from the group consisting of solvents, surfactants, emollients, preservatives, colorants, fragrances and mixtures thereof.

10. The method according to claim 1, wherein the pharmaceutical or pharmacologically active compound is selected from the group consisting of morphine, atropine, estradiol, and testosterone.

11. The method of claim 1 wherein the pharmacologically active compound is selected from the group consisting of narcotic analgesics including morphine and levorphanol, non narcotic analgesics including codeine and acetominophen, corticosteroids such as cortisone, anesthetics including propofol, antiemetics including scopolamine, sympathomimetic drugs including adrenaline and dopamine, antiepileptic drugs including fosphenytoin, anti-inflammatory drugs including ibuprofen, thyroid hormones and antithyroid drugs including thyroxine, phytochemicals including α-bisabolol, eugenol, silybin, soy isoflavones, iridoid glycosides including aucubin and catapol, sesquiterpene lactones including pseudoguaianolide from *Arnica chamissonis*, terpenes including rosmarinic acid and rosmanol, phenolic glycosides including the salicylates salicin, saligenin and salicylic acid, triterpenes taxasterol or α-lactucerol, and isolactucerol, taraxacoside, hydroquinones including arbutin, phenylalkanones including gingerols and shagaols, hypercin, and acylphloroglucides including xanthohumol, lupulone, humulone and 2-methyl-but-3-en-2-ol.

* * * * *